United States Patent
Zeligs

(10) Patent No.: US 8,552,052 B2
(45) Date of Patent: *Oct. 8, 2013

(54) USE OF DIINDOLYLMETHANE-RELATED INDOLES FOR THE TREATMENT AND PREVENTION OF RESPIRATORY SYNCYTIAL VIRUS ASSOCIATED CONDITIONS

(75) Inventor: Michael A. Zeligs, Boulder, CO (US)

(73) Assignee: BioResponse, L.L.C., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/164,488

(22) Filed: Jun. 20, 2011

(65) Prior Publication Data

US 2011/0250267 A1    Oct. 13, 2011

Related U.S. Application Data

(63) Continuation of application No. 11/322,803, filed on Dec. 30, 2005, now Pat. No. 7,989,486.

(60) Provisional application No. 60/640,301, filed on Dec. 30, 2004.

(51) Int. Cl.
    *A61K 31/405* (2006.01)
(52) U.S. Cl.
    USPC .................................................. 514/415
(58) Field of Classification Search
    USPC .................................................. 514/415
    See application file for complete search history.

(56) References Cited

U.S. PATENT DOCUMENTS

| | | |
|---|---|---|
| 5,635,215 A | 6/1997 | Boschetti et al. |
| 5,718,921 A | 2/1998 | Mahtiowitz et al. |
| 5,767,135 A | 6/1998 | Fernandez-Pol |
| 5,830,887 A | 11/1998 | Kelly |
| 5,895,787 A | 4/1999 | Arffmann et al. |
| 5,948,808 A | 9/1999 | Safe |
| 6,001,868 A | 12/1999 | Firestone |
| 6,086,915 A | 7/2000 | Zeligs et al. |
| 6,399,645 B1 | 6/2002 | Bell et al. |
| 6,410,570 B1 | 6/2002 | Fernandez-Pol |
| 6,416,793 B1 | 7/2002 | Zeligs |

(Continued)

FOREIGN PATENT DOCUMENTS

| | | |
|---|---|---|
| EP | 0566226 | 10/1993 |
| WO | WO 96/30347 | 3/1996 |

(Continued)

OTHER PUBLICATIONS

Aggarwal & Ichikawa, 2005, "Molecular targets and anticancer potential of indole-3-carbinol and its derivatives," Cell Cycle 4(9):1201-15.

(Continued)

*Primary Examiner* — Shengjun Wang
(74) *Attorney, Agent, or Firm* — Jones Day

(57) ABSTRACT

The present invention includes compositions and methods for the treatment and prevention of conditions associated with Respiratory Syncytial Virus (RSV) infection. RSV-associated conditions include acute infections in mammals, typically bronchiolitis and pneumonia, and post-infectious chronic respiratory conditions. In particular, the present invention describes new therapeutic and preventative uses for 3,3'-diindolylmethane (DIM), or a DIM-related indole, alone or in combination with an inhibitor of a membrane bound Epidermal Growth Factor Receptor (EGFR) inhibitors, to treat conditions associated with exposure to RSV.

24 Claims, 7 Drawing Sheets

(56) References Cited

U.S. PATENT DOCUMENTS

Figure 1:
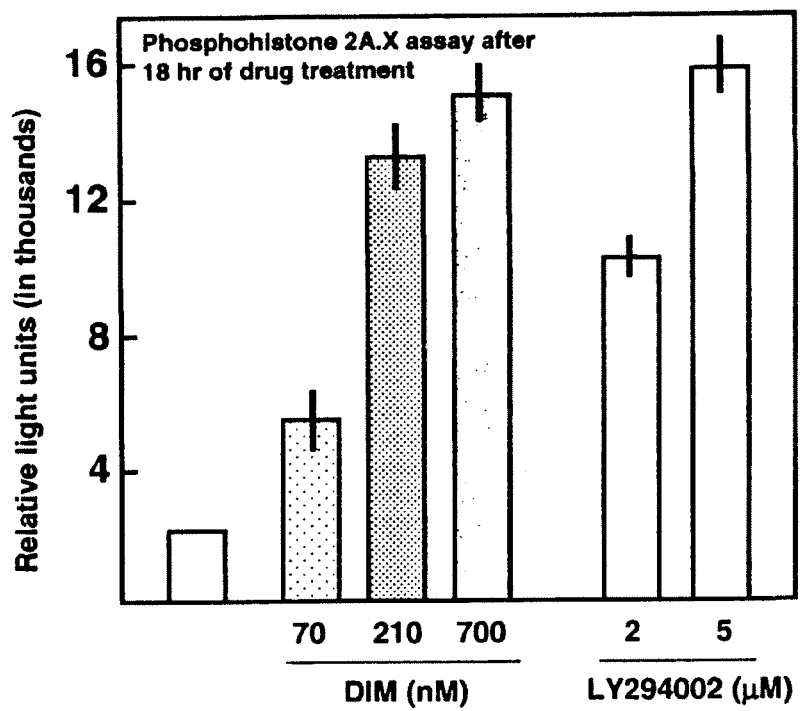

| | | | |
|---|---|---|---|
| 6,468,557 B1 | 10/2002 | Lezdey | |
| 6,477,229 B1 | 11/2002 | Grosser | |
| 6,534,085 B1 | 3/2003 | Zeligs | |
| 6,544,564 B1 | 4/2003 | Farley | 424/729 |
| 6,613,792 B1 | 9/2003 | Ellenberger et al. | |
| 6,656,963 B2 | 12/2003 | Firestone et al. | |
| 6,689,387 B1 | 2/2004 | Zeligs | |
| 6,800,655 B2 | 10/2004 | Jong et al. | |
| 7,348,352 B2 | 3/2008 | Zeligs | |
| 7,384,971 B2 | 6/2008 | Zeligs | |
| 7,384,972 B2 | 6/2008 | Zeligs | |
| 7,709,520 B2 | 5/2010 | Safe | |
| 7,989,486 B2 * | 8/2011 | Zeligs | 514/415 |
| 8,080,577 B2 | 12/2011 | Zeligs | |
| 8,236,848 B2 | 8/2012 | Zeligs | |
| 2001/0002393 A1 | 5/2001 | Palmer et al. | |
| 2002/0115708 A1 | 8/2002 | Safe | |
| 2002/0147155 A1 | 10/2002 | Foster et al. | |
| 2003/0096855 A1 | 5/2003 | Zeligs | |
| 2003/0211165 A1 | 11/2003 | Vogel | |
| 2003/0220377 A1 | 11/2003 | Chesworth | |
| 2003/0223956 A1 | 12/2003 | Goupil et al. | |
| 2004/0022869 A1 | 2/2004 | Chen et al. | 424/623 |
| 2004/0043965 A1 | 3/2004 | Jong et al. | |
| 2004/0072891 A1 | 4/2004 | Zeligs | |
| 2004/0156910 A1 | 8/2004 | Zeligs | |
| 2004/0225004 A1 | 11/2004 | Zeligs | |
| 2004/0235931 A1 | 11/2004 | Docherty | |
| 2004/0241192 A1 | 12/2004 | Valiante | 424/204.1 |
| 2005/0063903 A1 | 3/2005 | Zeligs | |
| 2005/0123560 A1 | 6/2005 | Sinnott | 424/195.18 |
| 2006/0100264 A1 | 5/2006 | Bjeldanes et al. | 514/414 |
| 2006/0229355 A1 | 10/2006 | Bjeldanes et al. | |

FOREIGN PATENT DOCUMENTS

| | | |
|---|---|---|
| WO | WO 96/33980 | 10/1996 |
| WO | WO 97/02266 | 1/1997 |
| WO | WO 97/30034 | 8/1997 |
| WO | WO 97/38983 | 10/1997 |
| WO | WO 99/55683 | 11/1999 |
| WO | WO 00/02857 | 1/2000 |
| WO | WO 00/31048 | 6/2000 |
| WO | WO 01/20990 | 3/2001 |
| WO | WO 01/24799 | 4/2001 |
| WO | WO 02/092575 | 11/2002 |
| WO | WO 2004/071425 | 5/2004 |
| WO | WO 2005/107747 | 11/2005 |
| WO | WO 2006/047716 | 5/2006 |
| WO | WO 2006/083458 | 8/2006 |

OTHER PUBLICATIONS

Banerjee et al., 2002, "Murine Coronavirus replication-induced p38 mitogen-activated protein kinase activation promotes Interleukin-6 production and virus replication in cultured cells," J. Virol. 76(12):5937-594.

Brandenburg et al., 2000, "Type-1-like immune response is found in children with Respiratory Syncitial Virus infection regardless of clinical severity," J.Med. Virol. 62:267-277.

Calabro et al, 2005, "Inhibition of Tumor-Necrosis-Factor-α induced endothelial cell activation by a new class of PPAR-γ: agonists. An in vitro study showing receptor-independent effects," J Vasc Res. 42:509-516.

Cannon et al., 1988, "Cytotoxic T Cells clear virus but augment lung pathology in mice infected with Respiratory Syncytial Virus," J. Exp. Med. 168:1163-1168.

Fernandez-Pol et al., 2001, "Antiviral, cytotoxic and apoptotic activities of picolinic acid on human immunodeficiency virus-1 and human herpes simplex virus-2 infected cells," Anticancer Res. 21(61):3773-6.

Krishnan et al., 2004, "Innate immune responses in Respiratory Syncitial Virus infections," Viral Immunol. 17(2):20-233.

Rahman et al., 2005, "Inhibition of nuclear translocation of nuclear factor-kB breast cancer cells contributes to 3,3'-Diindolylmethane-induced apoptosis in breast cancer cells," Cancer Res. 65:364-371.

Rogan, 2006, "The natural chemopreventive compound indole-3-carbinol: state of the science," In Vivo 20(2):221-8. Review.

Rutigliano & Graham, 2004, "Prolonged production of TNF-α exacerbates illness during Respiratory Syncitial Virus infection," J. Immunol. 173: 3408-3417.

Sehgal et al., 1988, "Regulation of the acute phase and immune responses in viral disease," J. Exp. Med. 167:1951-1956.

van Schaik et al., 1998, "Respiratory Syncitial Virus affects pulmonary function in BALB/c mice," 177(2):269-76.

van Schaik et al., 2000, "Role of Interferon gamma in the pathogenesis of primary Respiratory Syncytial Virus infection in BALB/c Mice," J. Med. Virol. 62:257-266.

van Woensel et al., 1997, "Randomised double blind placebo controlled trial of prednisolone in children admitted to hospital with Respiratory Syncitial Virus bronchiolitis," Thorax 52:634-637.

Yuhas et al, 1990, "Inhibition of tumor necrosis factor-induced cell killing by tryptophan and indole." Eur. Cytokine Net. 1: 35-40.

International Search Report, dated Aug. 6, 2007 of PCT/US05/47537 now published as WO2006/083458.

Written Opinion, dated Aug. 6, 2007 of PCT/US05/47537 now published as WO2006/083458.

Akkar et al., 2003, "Formulation of intravenous carbamazepine emulsions by SolEmuls technology," Eur J. Pharm Biopharm. 55:305-12.

Alberts et al., Molecular Biology of the Cell $2^{nd}$ ed,, 1989, Garland Publishing, Inc., New York, pp. 1193-1194, 1204-1206.

Anjun et al., 1988, "Spontaneous occurrence and experimental induction of leiomyoma of the ventral ligament of the oviduct of the hen," Res Vet Sci. 45:341-8.

Arbeit et al., "Chronic estrogen-induced cervical and vaginal squamous carcinogenesis in human papillomavirus type 16 transgenic mice", Apr. 1996, Proc Natl Acad Sci, USA 93:2930-2935.

Arici et al., 2003, "Expression, menstrual cycle-dependent activation, and bimodal mitogenic effect of transforming growth factor-beta1 in human myometrium and leiomyoma," Am J Obstet Gynecol. 188(1):76-83.

Auborn et al., 2000, "Treatment of Human Papillomavirus Gynecologic Infections", Clin Lab Med 20:407-22.

Auborn, 2002, "Therapy for recurrent respiratory papillomatosis," Antiviral Therapy, MTM Publications, London GB. 7(1):1-9.

Baugh et al., "Treatment of cervical dysplasia with indole-3-carbinol" in the Ray A. Barlow Scientific Symposium, Jan. 23, 1998, Shreveport : The Center for Excellence in Cancer Research, Treatment and Education, Louisiana State University Medical Center, Shreveport (LA), p. 3.

Bell et al., "Placebo-controlled Trial of Indole-3-Carbinol in the Treatment of Cervical Dysplasia", Abstracts Presented for the Thirtieth Annual Meeting of the Society of Gynecologic Oncologists Mar. 1999, Gynecol. Oncol. 72, 443-527 (Abstract 13).

Bell et al., "Placebo-Controlled Trial of Indole-3-Carbinol in the Treatment of CIN", 2000, Gynecologic Oncology 78:123-129.

Berto et al., 2003, "A comparative analysis of structure and spatial distribution of decorin in human leiomyoma and normal myometrium," Biochim Biophys Acta. 1619:98-112.

Bioresponse Letter, Dec. 29, 1998.

Bioresponse—DIM Indolplex Product Information Brochure, Dec. 15, 1998.

Bjeldanes et al., 1991, "Aromatic hydrocarbon responsiveness-receptor agonists generated from indole-3-carbinol in vitro and in vivo: comparisons with 2,3,7,8,-tetrachlorodibenzo-p-dioxin," Proc. Natl. Acad. Sci. USA 88:9543-9547.

Bonnesen et al., 2001, "Dietary indoles and isothiocyanates that are generated from cruciferous vegetables can both induce apoptosis and confer protection against DNA damage in human colon cell lines" Cancer Research, American Association for Cancer Research 61: 6120-6130.

Bradfield et al., 1987, "High-performance liquid chromatographic analysis of anticarcinogenic indoles in Brassica oleracea", J Agric Food Chem 35:46-49.

(56) References Cited

OTHER PUBLICATIONS

Bradfield et al., 1987, "Structure-Activity relationships of dietary indoles: a proposed mechanism of action as modifiers of xenobiotic metabolism," J Toxicol Environ Health 21:311-23.
Bradlow et al., 1999, "Multifunctional aspects of the action of indole-3-carbinol as an anyi-tumor agent," Annals of New York Academy of Sciences 889:204-213.
Bradlow et al., 1996, "2-hydroxyestrone: the 'good' estrogen" J Endocrin 150:S259-S265.
Brandi et al., 2003, "A new indole-3-carbinol tetrameric derivative inhibits cyclin-dependent kinase 6 expression, and induces G1 cell cycle arrest in both estrogen-dependent and estrogen-independent breast cancer cell lines," Cancer Res. 63(14):4028-36.
Buchwald et al., 1980, "Long-term, continuous intravenous heparin administration by an implantable infusion pump in ambulatory patients with recurrent venous thrombos," Surgery 88:507-16.
Cancer Medicine, 3rd edition, 1993, JF Holland ed., Lea & Febiger, Malvern, PA p. 1633.
Chang et al., 1999, "Cytostatic and antiestrogenic effects of 2-(Indol-3-ylmethyl)-3,3'-diindolylmethane, a major in vivo product of dietary indole-3-carbinol," Biochem. Pharmacol. 58:825-834.
Chapman et al., 2004, "Expression and deoxyribonucleic acid-binding activity of the nuclear factor kappaB family in the human myomertrium during pregnancy and labor," J Clin Endocrinol Metab. 89:5683-93.
Chen et al., 1998, "Aryl hydrocarbon receptor-mediated antiestrogenic and antitumorigenic activity of diindoylmethane", Carcinogenesis 19:1631-1639.
Chen et al., 2001, "Indole-3-carbinol and diindolylmethane induce apoptosis of human cervical cancer cells and in marine HPV 16-transgenic preoplastic cervical epithelium," J Nutr. 131:3294-302.
Dashwood, 1998, "Indole-3-carbinol: anticarcinogen or tumor promoter in brassica vegetables?" Chem Biol. Interact. 110( 1-2):1-5.
de Kruif et al., 1991, "Structure elucidation of acid reaction products of indole-3-carbinol: detection in vivo and enzyme induction in vitro," Chem Biol Interact. 80:803-15.
de Vet et al., 1994, "The role of cigarette smoking in the etiology of cervical dysplasia," Epidemiology 5:631-633.
During et al., 1989, "Controlled release of dopamine from a polymeric brain implant: in vivo characterization," Ann Neural. 25:351-56.
Exon, et al., 2000, "Dietary indole-3-carbinol alters immune functions in rats," J. Toxicol. Environ. Health A. 59(4):271-9.
Farman, 1975, "Benign smooth muscle tumors," S. Afr. Med. J. 19:1333-40.
Flake et al., 2003, "Etiology and pathogenesis of uterine leiomyomas: a review," Environ Health Perspect. 111:1037-54.
Flierman et al., 2005, "Rapid reduction of leiomyoma volume during treatment with the GnRH antagonist ganirelix," BJOG. 112:638-42.
Foster et al., 1989, "Influence of selection for increased body weight on the incidence of leiomyomas and leiomyosarcomas in Japanese quail," Poult Sci. 68:1447-53.
Gao et al., 2002, "Endocrine disruption by indole-3-carbinol and tamoxifen: blockage of ovulation," Toxicol Appl Pharmacol. 183:179-88.
Gillner et al., 1985, "Interactions of indoles with specific binding sites for 2,3,7,8-tetrachlorodibenzo-*p*-dioxin in rat liver," Mol Pharmacol 28:357-363.
Gooptu et al., 2000, "Treatment of viral warts with cimetidine: and open-label study," Clin. Exp. Dermatol. 25(3):183-5.
Green et al., 2000, "Pathogenesis and treatment of juvenile onset recurrent respiratory papillomatosis," Oto-Laryngologic Clinics of North America, W.B. Saunders, Philadelphia, US. 33(1):187-207.
Greenblatt el al., 1971, "Clinical studies with an anti-gonadotropin-danazol", Fertil Steril 22:102-112.
Hardman et al., "Goodman & Gilman's The Pharmacological Basis of Therapeutics" ($9^{th}$ ed, 1996) pp. 51 and 57-58.
Harrison-Woolrych et al., 1994, "Quantification of messenger ribonucleic acid for epidermal growth factor in human myometrium and leiomyomata using reverse transcriptase polymerase chain reaction," J Clin Endocrinol Metab. 78:1179-84.
Ho et al., 1998, "Urinary 2/16alpha-hydroestrone ratio: correlation with serum insulin-like growth factor binding protein-3 and a potential biomarker of breast cancer risk", Ann Acad Med Singapore 27:294-9.
Hong et al., 2002, "Bcl-2 family-mediated apoptotic effects of 3.3'-diindolylmethane (DIM) in human breast cancer cells," Biochem Phamacol. 61:1085-97.
Horiuchi et al., 2000, "HCG promotes proliferation of uterine leiomyomal cells more strongly than that of myometrial smooth muscle cells in vitro.," Mol Hum Reprod. 6-523-8.
Howard et al., 1989, "Intracerebral drug delivery in rats with lesion-induced memory deficits," J Neurosurg. 71:105-12.
Janmaat et al., 2003, "Small-molecule epidermal growth factor receptor tyrosine kinase inhibitors," Oncologist 8:576-86.
Janmaat et al., 2003, "The epidermal growth factor receptor pathway and its inhibition as anticancer therapy," Drugs Today (Barc) 39 Suppl C:61-80.
Jin et al., 1999, "Indole-3-carbinol prevents cervical cancer in human papillomavirus type 16 (HPV16) transgenic mice", Cancer Res 59:3991-7.
Komura et al., 1996, "Catecholestrogen as a natural antioxidant", Ann NY Acad Sci 786:419-29.
Langer et al., "New methods of drug delivery," Science 249:1527-1533.
Larsen-Su et al., 2001, "Transplacental exposure to indole-3-carbinol induces sex-specific expression of CYP1A1 and CYP1B1 in the liver of Fischer 344 neonatal rats," Toxicological Sci. 64:162-168.
Lee et al., 2004, "Inhibitory effects of Scutellaria barbata D. Don on human uterine leiomyomal smooth muscle cell proliferation through cell cycle analysis," Int Immunopharmacol. 4:447-54.
Lefebvre et al., 2002, "Clinical Practice Gynaecology Committee, Society for Obstetricians and Gynaecologists of Canada. The management of uterine leiomyomas," J Obstet Cynaecol Can. 25:396-418.
Leong et al., 2004, "Potent ligand-independent estrogen receptor activation by 3,3'-diindolylmethane is mediated by cross talk between the protein kinase A and mitogen-activated protein kinase signaling pathways," Mol Endocrinol. 18:291-302.
Levy et al., 1985, "Inhibition of calcification of bioprosthetic heart valves by local controlled-release diphosphonate," Science 228:190-192.
Liehr et al., 1995, "4-Hydroxylation of estradiol by human uterine myometrium and myoma microsomes: implications for the mechanism of uterine tumorigenesis," Proc Natl Acad Sci USA. 92:9220-4.
Liu et al., 1994, "Indolo[3,2-b]carbozole: a dietary-derived factor that exhibits both estrogenic and estrogenic activity," J. Natl. Cancer Inst. 86:1758-1765.
Loria RM et al., 1990, "Immune response facilitation and resistance to virus and bacterial infectionis with dehydroepiandrosterone (DHEA)," Biologic Role of Dehydroepiandrosterone, pp. 107-130.
Loub et al., 1975, "Aryl hydrocarbon hydroxylase induction in rat tissues by naturally occurring indoles of cruciferous plants," J. Natl. Cancer Inst. 54:985-988.
Marshall et al., 1997, "Variation in the incidence of uterine leiomyoma among premenopausal women by age and race," Obstet Gynnecol. 90:967-73.
Michnovicz et al., 1986, "Increased 2-hydroxylation of estradiol as a possibe mechanism for the anti-estorgenic effect of cigarette smoking," N Engl J Med 315:1305-1309.
Michnovicz et al., 1988, "Increased urinary catechol estrogen excretion in female smokers," Steroids 52:69-83.
Michnovicz et al., 1991, "Cimetidine inhibits catechol estrogen metabolism in women," Metabolism 40(2):170-74.
Michnovicz et al., 1997, "Changes in levels of urinary estrogen metabolites after oral indole-3-carbinol treatment in humans", J Natl Cancer Inst 89:718-23.
Morfin R et al., 1994, "Pregnenolone and dehydroepiandrosterone as precursors of native 7-hydroxylated metabolites which increase the immune response in mice," J of Steroid Biochemistry and Molecular Biology, Elsevier Science Ltd., Oxford, GB, vol. 50(1/2) Jul. 1994, pp. 91-100.

(56) References Cited

OTHER PUBLICATIONS

Muzandu et al., 2005, "Lycopene and beta-carotene ameliorate catechol estrogen-mediated DNA damage," Jpn J Vet Res. 52:173-84.
Nair, 2003, "Contemporary management of fibroids," Ann Acad Med Singapore, Ann Acad Med. Singapore 32:615-23.
Ponten and Guo, 1998, "Precancer of the Human Cervix", Cancer Surveys 32:201-229.
Langer and Peppas, 1983, "Chemical and physical structure of Polymers as carriers sfor controlled release of bioactive agents: a review," J. Macromol Sci Rec Macromol. Chem 23:61-126.
Rein, 2000, "Advances in uterine leiomyoma research: the progesterone hypothesis," Environ Health Perspect. 108 Suppl 5:791-3.
Riby et al., 2000, "Ligand-independent activation of estrogen receptor function by 3,3'-diindolylmethane in human breast cancer cells," Biochem. Pharmacol. 60:167-177.
Ritter el al., 2001, "Oxidations of 17beta-estradiol and estrone and their interconversions catalyzed by liver, mammary gland and mammary tumor after acute and chronic treatment of rats with indole-3-carbinol or beta-naphthoflavine," Can. J. Physiol. Pharmacol. 79(6):519-32.
Rosen et al., 1998, "Preliminary results of the use of indole-3-carbinol for recurrent respiratory papillomatosis", Otolaryngol Head Neck Surg 118:810-5.
Sah et al., 2004, "Epigallocatechin-3-gallate inhibits epidermal growth factor receptor signaling pathway. Evidence for direct inhibition of ERK1/2 and AKT kinases," J Biol Chem. 279:12755-62.
Sahin et al., 2004, "Lycopene supplementation prevents the development of spontaneous smooth muscle tumors of the oviduct in Japanese quail," Nutr Cancer 50:181-9.
Saudek et al., 1989, "A preliminary trial of the programmable implantable medication system for insulin delivery," New Engl. J. Med. 321:574-79.
Schneider et al., "Abnormal oxidative metabolism of estradiol in women with breast cancer", 1982, Proc Natl Acad Sci USA 79:3047-52.
Schwartz et al., 1995, "Cancer prevention with dehydroepiandrosterone and non-androgenic structural analogs," Journal of Cellular Biochemistry, Suppl. 22, 210-217.
Schwartz et al., 1998, "Use of transvaginal ultrasonography to monitor the effects of tamoxifen on uterine leiomyoma size and ovarian cyst formation," J Ultrasound Med. 17:699-703.
Sefton, 1987, "Implantable pumps," CRC Crit Ref., Biomed Eng. 14:201-240.
Sepkovic et al., 2001, "Quantitative Determination of 3,3'-Diindolymethane in the urine of individuals receiving indole-3-carbinol," Nutr Cancer. 41(1-2):57-63.
Sharma et al., 2001, "Inhibitory effect of silibinin on ligand binding to erbB1 and associated mitogenic signaling, growth, and DNA synthesis in advanced human prostate carcinoma cells," Mol Carcinog. 30:224-36.
Shilling et al., 2001, "3,3'-diindolylmethane, a major condensation product of indole-3-carbinol, is a potent estrogen in the rainbow trout," Toxicology and Applied Pharmacology 170:191-200.
Smail et al., 1999, "Tyrosine kinase inhibitors. 15, 4-(Phenylamino)quinazoline and 4-(phenylamino)pyrido[d]pyrimidine acrylamides as irreversible inhibitors of the ATP binding site of the epidermal growth factor receptor," J Med Chem. 42:1803-1815.
Spies et al., 2002, "Complications after uterine artery embolization for leiomyomas," Obstet Gynecol. 100:873-80.
Stewart et al., 2004, "Resveratrol antagonizes EGFR-dependent Erk1/2 activation in human androgen-independent prostate cancer cells with associated isozyme-selective PKC alpha inhibition," Invest. New Drugs 22:107-117.
Stresser et al., 1995, "Mechanisms of tumor modulation by indole-3-carbinol: disposition and excretion in male fisher 344 rats," Drug Metabolism and Disposition 23:965-975.
Stresser et al., 1995, "The anticarcinogen 3,3'-Diindolyl-methane is an inhibitor of cytochrome P-450," J. Biochem. Toxicol. 10(4):191-201.
Strobelt et al., 1994, "Natural history of uterine leiomyomas in pregnancy," J Ultrasound Med. 13:399-401.
Supplemental Search Report from European Patent Application No. 05857257.9, dated May 19, 2008.
Telimaa et al., 1987, "Placebo-controlled comparison of danazol and high-dose medroxyprogesterone acetate in the treatment of endometriosis", Gynecol Endocrinol 1:13-23.
Thomas et al., 1987, "Impact of gestrinone on the course of asymptomatic endometriosis" Br Med J 294:272.-74.
Thomas et al., 2002, "Respiratory syncytial virus inhibits apoptosis and induces NF-kappa B activity through a phosphatidylinositol 3-kinase-dependent pathway," J Biol Chem. 277(1):492-501.
Tse et al., 1987, "Disposition of alpha-[(dimethylamino)methyl]-2-(3-ethyl-5-methyl-4-isoxazolyl)-1H-indole-3-methanol (59-801), a hypoglycaemic agent in rats, dogs and monkeys," Xenobiotica, 17(6):741-9.
Tzingounis et al., 1997, "Modern approach to endometriosis," Annals New York Acad Sci. 816:320-330.
Venkatachalam et al., 2004, "Medical management of uterine fibroids with medroxyprogesterone acetate (Depo Provera): a pilot study," J Obstet Gynaecol. 24:798-800.
Walboomers et al., 1999, "Human papillomavirus is a necessary cause of invasive cervical cancer worldwide," J. Pathol. 189:12-19.
Woodburn et al, 1999, "The epidermal growth factor receptor and its inhibition in cancer," Pharmacol. Ther. 82:241-250.
Xu et al., 2002, "Stable isotope dilution high-performance liquid chromatography-electrospray ionization mass spectrometry method for endogenous 2- and 4-hydroxyestrones in human urine," J Chromatogr B Analyt Technol Biomed Life Sci. 780:315-30.
Yuan F et al., 1999, "Prevention of Papillomavirus initiated cancer by the phytochemical Indole-3-Carbinol", Proceedings of the 17th International Papillomavirus Conference, Jan. 9-15, p. 73.
Zeligs et al., 2002, "Absorption-enhanced 3,3-dindolylmethane: human use in HPV-related, benign and pre-cancerous conditions," Proceedings of the Annual Meeting of the American Association for Cancer Research, New York, NY vol. 43, Mar. 2002, pp. 664, Abstract 3198.
Zeligs, 1998, "Diet and Estrogen Status: The Cruciferous Connection", J Med Food 1:67-82.
Smith Neutrophils, host defense, and inflammation: a double-edged sword, J. Leukocyte Biology, 1994, vol. 56, pp. 672-686.

\* cited by examiner gRSV = Recombinant RSV expressing GFP.
Assay = Real-time fluorescence measurement of live infected cells.
□ = Caspase-8 inhibitor; Δ = Caspase-3 inhibitor; × = Pan-caspase inhibitor.

USE OF DIINDOLYLMETHANE-RELATED INDOLES FOR THE TREATMENT AND PREVENTION OF RESPIRATORY SYNCYTIAL VIRUS ASSOCIATED CONDITIONS

This application is a continuation of U.S. application Ser. No. 11/322,803, filed Dec. 30, 2005 now U.S. Pat. No. 7,989,486, which claims the benefit of U.S. Provisional Application No. 60/640,301, filed Dec. 30, 2004, each of which is herein incorporated by reference in its entirety.

1. FIELD OF THE INVENTION

The present invention includes methods and compositions for the treatment and prevention of conditions associated with Respiratory Syncytial Virus (RSV) infection. RSV-associated conditions include acute infections in mammals, typically bronchiolitis and pneumonia, and post-infectious chronic respiratory conditions. The present invention describes new therapeutic and preventative uses for 3,3'-diindolylmethane (DIM), or synthetic DIM-related indoles, in RSV-associated conditions. The present invention also provides for the use of Epidermal Growth Factor Receptor (EGFR) tyrosine kinase inhibitors in combination with DIM or a DIM-related indole for treatment of RSV-associated conditions, particulary severe RSV-associated conditions. In other embodiments, DIM or a DIM-related indole, alone or in combination with an EGFR inhibitor, is used in combination with other known anti-viral compounds and anti-RSV specific antibodies in the treatment of RSV-associated conditions. In certain embodiments, the compositions of the invention can be used in combination with anti-retroviral agents, anti-inflammatory agents or cancer chemotherapeutics for the treatment of RSV-associated conditions that accompany Human Immunodeficiency Virus (HIV) infection, cancer, or aquired immunodeficiency states seen following bone marrow transplantation, organ transplantation, and immunosuppressive treatment of arthritis and autoimmune disease.

2. BACKGROUND OF THE INVENTION

2.1 The Rote of Respiratory Syncytial Virus (RSV) in Disease 2.1.1 Importance of RSV as a Pathogen RSV is a pathogenic agent in a number of human and animal diseases. RSV is a pleomorphic, enveloped, cytoplasmic virus containing single-stranded, negative-sense RNA. RSV is classified in the genus *Pneumovirus*, which belongs to the family Paramyxoviridae. The Paramyxoviridae family also include two other genera important in causing human disease, *Paramyxovirus* (containing, e.g., parainfluenza virus [types 1, 2, and 3] and mumps virus) and *Morbillivirus*, the cause of measles. RSV enters into host cells (primarily the conjunctival, naso-pharyngeal, and respiratory epithelia) by cell-surface fusion. Infection of lung epithelial cells leads to viral replication and induction of an inflammatory response characterized by the production of chemokines and cytokines.

2.1.1.1 The Role of RSV in Human Disease

RSV is an important pathogen in infants, young children, and immunocompromised adults. Worldwide, RSV is the most common cause of bronchiolitis and pneumonia associated hospitalization of children less than two years of age. Early, severe RSV infections cause long-term morbidity and mortality by increasing the risk for recurrent wheezing and asthma symptoms throughout childhood. Persistent RSV infection and/or persistent RSV-related inflammation increases the predisposition to other forms of pneumonia, including streptococcal pneumonia (Hament et al., 2004, Pediatr Res. 55(6):972-8). Conjunctival infection with RSV also occurs and evidence indicates that RSV conjuntival infection is an important contributor to subsequent chronic, allergic conjunctivitis (Fujishima, 2002, Cornea 21(2 Suppl 1):S39-45). RSV is found ubiquitously in the environment, producing more frequent infections on a yearly basis during the Winter months.

RSV presents a greater risk to immunocompromised children and adults, and the elderly. In the United States alone, there is a relatively large population of infants and children, of about 100,000 to 200,000, at high risk of developing severe or fatal RSV illness. The high risk population includes infants born prematurely, infants in the first 6 months of life, and children with bronchopulmonary dysplasia, congenital heart disease, cystic fibrosis, cancer or various forms of immunodeficiency, as well as adults and children immunosuppressed prior to and following bone marrow transplantation.

In the United States, RSV infection leads to more than 90,000 yearly hospitalizations and a 2% mortality rate among infants nationwide (Le Calvez et al., 2004, Virol. J. 1:12). Approximately two-thirds of infants are infected with RSV during the first year of life and approximately 95% of children test seropositive for RSV by the age of two. Unfortunately, even natural RSV infection produces limited immunity and recurrent infections, although less severe, occur in children and adults. In addition, RSV has been identified as a possible cause of crib death in infants.

2.1.1.2 The Role of RSV in Animal Diseases

Respiratory syncytial virus can infect cattle, sheep and goats. In cows, bovine Respiratory Syncytial Virus (bRSV) is a major cause of respiratory disease (Antonis et al., 2003, J Virol 77:12067-12073; Stott et al., 1985, Arch. Virol. 84:1-52). Primary infection by bRSV can cause severe lower respiratory tract disease in susceptible cattle, especially in calves and yearlings. For example, the virus causes an acute interstitial pneumonia with alveolitis and bronchiololitis (Van Den high et al., 1982, Res. Vet. Sci. 33:152-158). In outbreaks, fatality rates can be as high as 20% (Merck Vet. Manual, 8$^{th}$ ed.).

2.1.2 The Pathobiology of RSV Infection Includes Inhibition of Apoptosis

Apoptosis is the process of programmed cell death by which epithelial cells are naturally eliminated. Accelerated apoptosis in response to viral infection of epithelial surfaces serves as a defense mechanism protecting the host. However, some viruses have evolved molecular mechanisms to suspend apoptosis in cells in order to provide a better opportunity for the virus to successfully complete viral replication and release mature viral progeny. Cultured airway epithelial cells display little or no cytotoxic effects early in the course of RSV infection. Instead, RSV activates cell survival and gene transcription pathways which suspend apoptosis, and maintain cell viability until mature viral production has been accomplished. RSV produces an early activation of anti-apoptotic cell signaling, including phosphatidylinositide-3-kinase (PI 3-K) and downstream Akt (PKB/Akt) in cultured airway epithelial cells (Thomas et al., 2002, J. Biol. Chem. 277:492-501). Activated PKB/Akt acts intracellularly to phosphorylate and regulate the function of many cellular proteins involved in processes that include suppression of apoptosis and cell proliferation. Recent evidence suggests that PKB/Akt becomes activated in response to diverse stimuli in addition to growth factors including, hormones, extracellular matrix components, and viral infections such as the human cytomegalovirus (HCMV) (Yu et al., 2002, J Virol. 76:3731-8). In addition, PKB/Akt is frequently constitutively active in many types of human cancer.

Most recently, early RSV infection of cultured epithelial cells was shown to be associated with activation of the HER1 class of Epidermal Growth Factor Receptors (EGFR). Activation of EGFR by RSV triggered activation of associated MAP kinase activity and an increase the production of anti-apoptotic proteins (Monick et al., 2005, J. Biol. Chem. 280 (3):2147-58). This is similar to HCMV which produces virus specific proteins which inhibit the cellular process of apoptosis (Goldmacher et al., 1999, Proc Natl Acad Sci USA 96:12536-41). HCMV immediate-early (IE) proteins activate anti-apoptotic cellular growth and survival pathways including MAPK activation following infection (Rodems et al., 1998, J Virol. 72:9173-80).

2.1.3 Current Approaches to Prevention of RSV Infections.

Currently, no approved vaccines exist to prevent RSV infection. Vaccine development against hRSV (human RSV) and bRSV has been hampered by a dramatic hRSV vaccine failure in the 1960s: vaccination with formalin-inactivated (FI), alum-adjuvanted virus predisposed children to a far more serious, and sometimes lethal, form of RSV infection (Kim et al., 1969, Am. J. Epidemiol. 89:422-434). Subsequently, it was found in the 1970s that a similarly inactivated bRSV vaccine could induce strikingly similar immunopathology in bRSV-infected calves (West et al., 1999, Vaccine 17:809-820). Moreover, some inactivated veterinary vaccines were withdrawn from the market after safety problems were discovered.

Since there is no RSV vaccine available for hRSV or bRSV, approaches to the transfer of passive immunity to RSV have been developed. One prophylactic strategy entails periodic intravenous inoculation of human IgG prepared from pooled plasma. Because of the large quantity of globulin required (1 to 2 gm per kg) and the need to administer this material intravenously in the clinic or hospital over a 2 to 4 hour interval every month during the fall, winter and early spring, this strategy is expensive and not practical.

Anti-viral antibodies have been used successfully to transfer passive immunity. RespiGam™ (respiratory syncytial virus immune globulin or RSV-IG) and Synagis™ (Palivizumab [MedImmune]) have been used in children less than two years of age with high-risk factors (Le Calvez et al., 2004, Virol. J. 1:12). Palivizumab is an IgG1 monoclonal antibody that selectively binds to the RSV surface glycoprotein F. The drug specifically inhibits RSV replication by preventing the virus from fusing with the respiratory endothelial cell membrane. Using monthly intramuscular injections, Palivizumab has been shown to reduce the rate of hospitalization of at-risk infants by about 55% in clinical studies and now serves as the primary medical means of RSV prevention. However, the availability of antibody based prophylactic intervention does not reduce the need for effective medical intervention, where treatment, preferably oral or intravenous, can be directed to symptomatic cases of RSV and to individuals immediately following exposure to RSV.

2.1.4 Current Approaches to Treatment of RSV Infections

Aerosolized ribavirin/Virazole (1-beta-D-ribofuranosyl-1, 2,4-triazole-3-carboxamide [Valeant Pharmaceuticals, Costa Mesa, Calif.]) is a nucleoside analog with activity against RSV in vitro and in vivo. Ribavirin is the first and only approved agent for the treatment of respiratory syncytial virus (RSV) infection. However, the clinical use of ribavirin is controversial. Although ribavirin-treated patients appear to be subjectively improved, no benefit in terms of decreased morbidity and mortality has been established in contolled clinical trials (Law et al., 1997, Pediatrics 99:E7). Furthermore, the drug has been found to be teratogenic, carcinogenic, and/or mutagenic. Because of its unique mode of administration by aerosol, environmental exposure of healthcare personnel and other patients may occur. Although administration in mechanically ventilated patients decreases the amount of ribavirin liberated into the atmosphere, the drug crystallizes in the endotracheal tube, occasionally resulting in reduced ventilation. The lack of data documenting efficacy, safety concerns, and the above environmental concerns reduce the usefulness of ribavirin for hRSV treatment in humans. Its use in bRSV is not practical.

Besides ribavirin, only one other small molecule drug, the triazine RFI 641 (Wyeth Pharmaceuticals, Pearl River, N.Y. [U.S. Pat. No. 5,852,015]), has reached Phase II clinical testing for the treatment of RSV. RD3-0028 (Rational Drug Design Laboratories, JP) is a benzodithiin derivative, which, when administered to RSV-infected mice by aerosol, has reduced viral titers at lower doses than ribavirin (Sudo et al., 2001, Microbiol Immunol. 45:531-7). Both RFI 641 and RD3-0028 require delivery by aerosol, which limits use in the wide spectrum of RSV disease better treated with injectable and/or oral formulations.

2.2 Cruciferous Indoles 2.2.1 Natural Indole Compounds can Influence Apoptosis

Cruciferous vegetables contain a family of plant protective compounds called glucosinolates which give rise to active compounds with indole rings exemplified by indole-3-carbinol (I3C). Oral ingestion of I3C results in the gastric conversion of I3C into at least twenty acid condensation products, many of which are bioavailable, the most prevalent of which include CTR (cyclic trimer; 5,6,11,12,17,18-hexahydrocyclonona[1,2-b:4,5-b':7,8-b"]triindole), HI-IM (1-(3-hydroxymethyl)-indolyl-3-indolylmethane), DIM (diindolylmethane), ICZ (indolocarbazole) and LTr-1 (linear trimer; [2-(indol-3-ylmethyl)-indol-3-yl]indol-3-ylmethane) (Stresser et al., 1995, Drug Metabolism and Disposition 23:965-975). The fact that there are many non-DIM acid condensation products of I3C, produced in vivo at equal or greater levels as DIM, which can be responsible for I3C's activity, requires that biologic activities of individual condensation products like DIM be demonstrated directly.

As one of many products derived from I3C, DIM is also present in cruciferous plants following release of I3C. Once formed, DIM is stable in acid. In cell culture, isolated DIM has been shown to have apoptosis promoting effects in both estrogen-dependent and independent breast cancer cells (Hong et al., 2002, Biochem Pharmacol. 63:1085-97). In animals, orally administered DIM inhibits the growth of certain chemically induced forms of breast cancer (Chen et al., 1998, Carcinogenesis 19:1631-9). Recently, DIM has been shown to specifically induce apoptosis in Human Papilloma Virus (HPV) oncogene altered cervical cancer cell lines (Chen et al., 2001, J Nutr. 131:3294-302). This cell culture work demonstrated that DIM was more active than I3C in inducing markers of apotosis. Other non-DIM I3C condensation products were not tested. Further work has utilized DIM in the cell culture of prostate cancer cell lines demonstrating it to have anti-androgen activity similar to non-indole antiandrogen drugs (Le et al., 2003, J Biol Chem. 278:21136-45). In vivo studies in mice suggest that expected effective plasma levels of DIM are not easily achieved in humans (Anderton et al., 2004, Drug Metab Dispos. 32:632-8).

While shown to be an anti-androgen in prostate cancer cells, DIM has also been shown to be estrogenic in breast cancer cells (Riby et al., 2000, Biochem. Pharmacol. 60:167-177) and in rainbow trout, a model of carcinogenesis relevant to viral disease in humans (Shilling et al., 2001, Toxicology and Applied Pharmacology 170:191-200). Since estrogenic effects inhibit apoptosis, DIM may actually enhance estrogen related growth and survival of virally infected cells. Based on the conflicting results of DIM activity in cell culture studies and estrogenic activity in vivo, it is difficult to predict DIM's effects in vivo on cancer or virus-related processes. Finally, DIM has been shown to activate the Mitogen Activated Protein Kinase (MAPK) cell signaling pathway in cell culture (Leong et al., 2004, Mol Endocrinol. 18:291-302). Activated MAPK is associated with cancer promotion, cancer cell survival, and inhibition of apoptosis. These properties of DIM suggest that DIM would not be useful for treating RSV infections. Thus, the prior scientific literature teaches that DIM is not a likely acid condensation product of I3C which may be responsible for I3C's anti-HPV activity, and that DIM itself is not a likely candidate for anti-RSV activity.

2.3 Need for Better Therapy for RSV-Associated Conditions

Immunocompetent humans and animals suffering from diseases caused by RSV are typically treated with supportive care only. In hospitalized patients, lack of efficacy and toxicity associated with ribavirin aerosol treatment requires the development of safer, more effective, and more convenient RSV treatments. The serious and life-threatening nature of RSV infection in immunocompromised patients make the lack of adequate medical therapy for RSV an important unmet need.

One approach, that has not been utilized in RSV-associated disease, would be to selectively induce apoptosis in early RSV infection to cause programmed death of infected cells prior to full replication and release of mature virus particles.

3. SUMMARY OF THE INVENTION

The present invention concerns treatment and prevention for RSV-associated conditions. The invention provides methods of use of diindolylmethane (DIM) and DIM-related indoles, alone and in combination with various EGFR inhibitors, in the prevention and treatment of RSV-associated conditions. Methods are also provided that use DIM, or DIM-related indoles, optionally with EGFR inhibitors, including, but not limited to, monoclonal antibodies and small molecule EGFR inhibiting drugs, to treat RSV infections, such as RSV acute infections, and post-infectious chronic inflammatory conditions, and prevent RSV-associated chronic pulmonary and allergic sequellae. Examples of RSV acute infections, include, but are not limited to, pharyngitis, croup, otitis media, bronchiolitis, pneumonia, and conjunctivitis. Examples of post-infectious chronic inflammatory conditions include, but are not limited to, chronic wheezing, asthma, allergic asthma, chronic sinusitis, allergic rhinitis and allergic conjunctivitis. The methods of the invention are used for the prevention and treatment of RSV infections in animals, particularly cattle, and humans. Methods according to the invention include preventing or treating a RSV infection and/or RSV-associated condition comprising administering to a subject in need thereof a therapeutically effective amount of DIM, or a DIM-related indole, a Epidermal Growth Factor Receptor (EGFR) inhibitor, or a combination of DIM, or a DIM-related indole, and an EGFR inhibitor. In a preferred embodiment, DIM, or a DIM-related indole, is administered orally.

In certain embodiments, these methods employ structurally-related, synthetically-derived, substituted diindolylmethane compounds. In a particular embodiment, the one or more DIM-related indoles of the invention are selected from the group consisting of I3C, 3,3'-diindolylmethane (DIM), hydoxylated DIMs, methoxylated DIMs, 2-(Indol-3-ylmethyl)-3,3'-diindolylmethane (LTR), hydroxylated LTRs, methoxylated LTRs, 5,5'-dimethylDIM (5-Me-DIM), 2,2'-dimethylDIM (2-Me-DIM), 5,5'-dichloroDIM (5-Cl-DIM), imidazolyl-3,3'-diindolylmethane, nitro-substituted imidazolyl-3,3'-diindolylmethanes, 2,10-dicarbethoxy-6-methoxy-5,7-dihydro-indolo-[2,3-b]carbazole, 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole, and 2,6-dicarbethoxy-3,3'-dimethyl-13,14-diindolylmethane. In a preferred embodiment, the DIM-related indole is DIM. In a more preferred embodiment, DIM is processed DIM. DIM is processed to provide for enhanced gastrointestinal absorption and for use in intravenous suspensions/emulsions.

In certain embodiments, the EGFR inhibitor is an EGFR-specific small molecule drug or an EGFR specific antibody. Examples of EGFR-specific small molecule drugs include, but are not limited to, gefitinib, ZD6474, erlotinib, lapatinib, GW-2016, imatinib myesylate, EKB-569, cancertinib, semaxanib, SU11248, SU6669, vatalanib, PKI-166, and CEP-7055. Examples of EGFR specific antibodies include cetuximab, trastuzumab, MDX-210, ABX-EGF, TheraCIM, panitumumab, EMD-72000, bevacizumab, and ranibizumab.

In a particular embodiment, the DIM-related indole and a EGFR inhibitor are administered simultaneously. In another embodiment, the DIM-related indole and a EGFR inhibitor are administered within a short time of one another, for example, 30 seconds, 1 minute, 5 minutes, 15 minutes, 30 minutes, 1 hour, 4 hours, 8 hours, 12 hours or 24 hours of one another.

In an additional embodiment, a DIM-related indole, with or without an EGFR inhibitor, is administered in conjunction with differentiation promoting agents which help RSV infected epithelial cells develop into more completely differentiated and therapeuticially sensitive cells. Differentiation promoting agents include Vitamin-D, Vitamin-D derivatives, calcitriol, Vitamin-A (retinoids), retinoid derivatives, and granulcyte/macrophage colony stimulating factors including recombinant human Filgrastim and Sargramostim.

In an additional embodiment, a DIM-related indole, with or without an EGFR inhibitor, is administered in conjunction with one or more of a farnesyl transferase inhibitor, a proteosome inhibitor, a RAF inhibitor, an endoplasmic reticulum stress inducer, RSV anti-viral drug, immune stimulating beta glucan, or resveratrol. Examples of RSV anti-viral drugs, include, but are not limited to, an RSV-vaccine, anti-RSV immunoglobulin, hAnti F-glycoprotein, anti-RSV monoclonal antibody, plant flavinoid, benzoditin, ribavirin, ganciclovir, valganciclovir, cidofovir, and phosphocarnet.

The invention further provides pharmaceutical compositions, for example, a pharmaceutical composition comprising a therapeutically effective amount of the combination of DIM or a DIM-related indole and an EGFR inhibitor. In particular embodiments, the composition is formulated for oral, parenteral, aerosol, or topical administration.

4. BRIEF DESCRIPTION OF THE DRAWINGS

FIG. 1. DIM treatment promotes apoptosis in RSV infected pulmonary epithelial cells. 18 hour treatment of A549 pulmonary epithelial cells using nanomolar (nM) concentrations of DIM caused a significant, dose-related increase in cells undergoing apoptosis. Promotion of apoptosis by DIM was more potent than that seen with LY294002, a chemical promoter of apoptosis and inhibitor of Phosphoinositol-3-kinase (PI3K).

Figure 2:
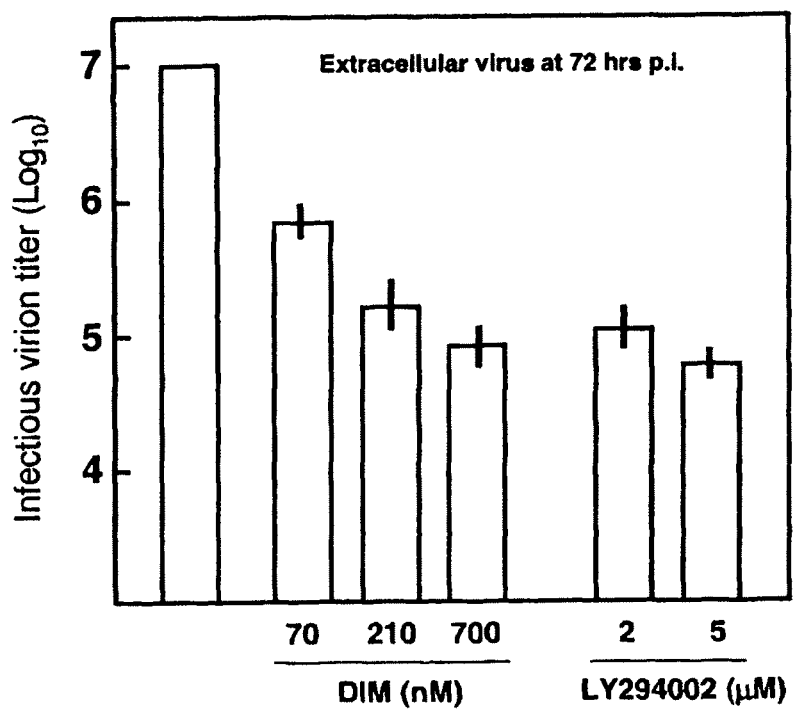

FIG. 2. DIM treatment inhibits RSV yield from infected A549 cells. 72 hour treatment of A549 pulmonary epithelial cells using nanomolar (nM) concentrations of DIM resulted in significantly reduced viral replication and production of extracellular, progeny RSV viral particles. Reduction of RSV replication by DIM was comparable to that seen with higher concentrations of LY294002, a chemical promoter of apoptosis and inibibitor of Phosphoinositol-3-kinase (PI3K).

Figure 3:
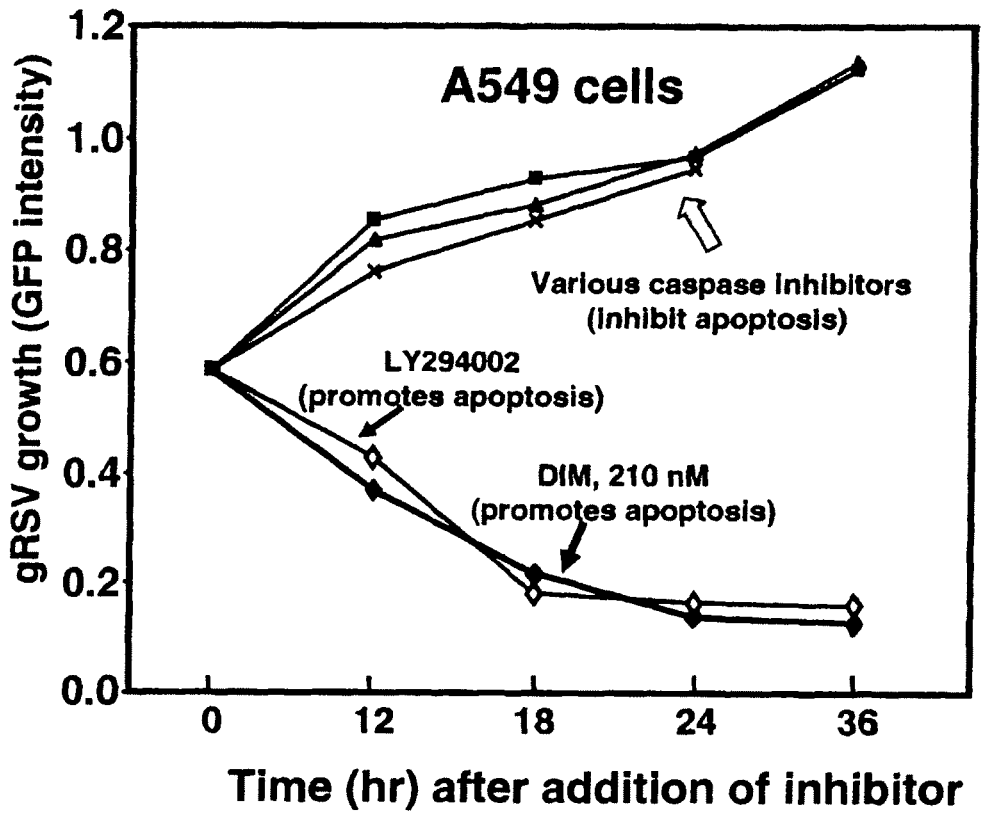

FIG. 3. Earlier apoptosis of DIM-treated cells reduces intracellular RSV growth. Beginning 12 hours after addition of nanomolar (nM) DIM, the presence of intracellular RSV activity was significantly reduced in cultured A549 cells. Similar reductions in RSV activity were seen using LY294002, a chemical inducer of apoptosis. Caspase inhibitors, which reduce apoptosis, served as a positive control and produced an increase in intracellular RSV activity.

Figure 4:
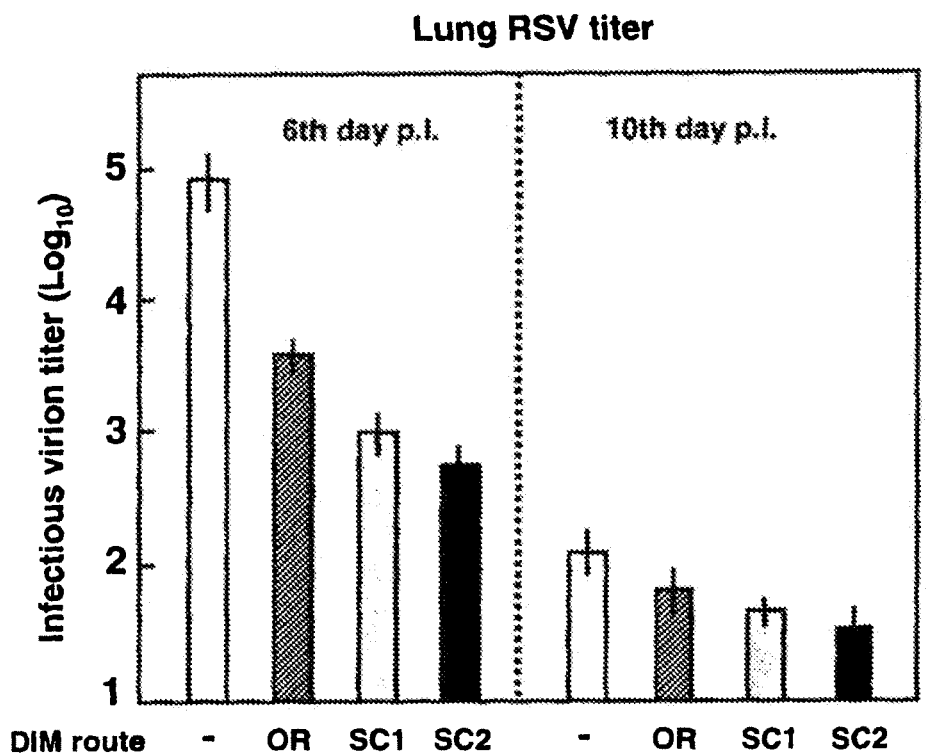

FIG. 4. DIM treatment (Oral and SC) in BALB/c mice inhibits RSV growth in lung. Oral and subcutaneous (SC) administration of DIM significantly reduced the intrapulmonary replication of nasally administered RSV virus at 6 days post infection (pi). SC administered DIM still showed a significantly reduced pulmonary viral count at 10 days pi, compared to vehicle treated, RSV-infected controls. "OR"— orally treated DIM group (250 mg/kg/day from absorption enhanced DIM); "SC1"—1Low dose parenteral DIM group (15 mg/kg/day), injected SC once daily with DIM suspension; "SC2"—high dose DIM Group (150 mg/kg/day), injected SC once daily with DIM suspension.

Figure 5A:
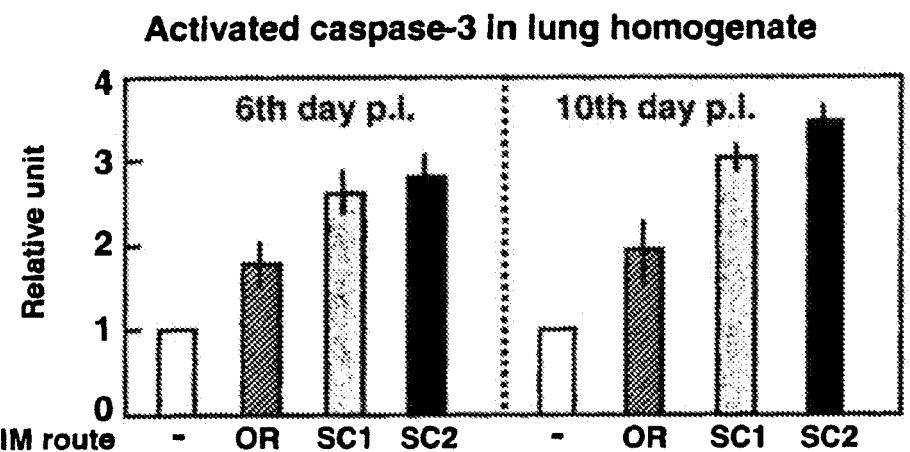
Figure 5B:
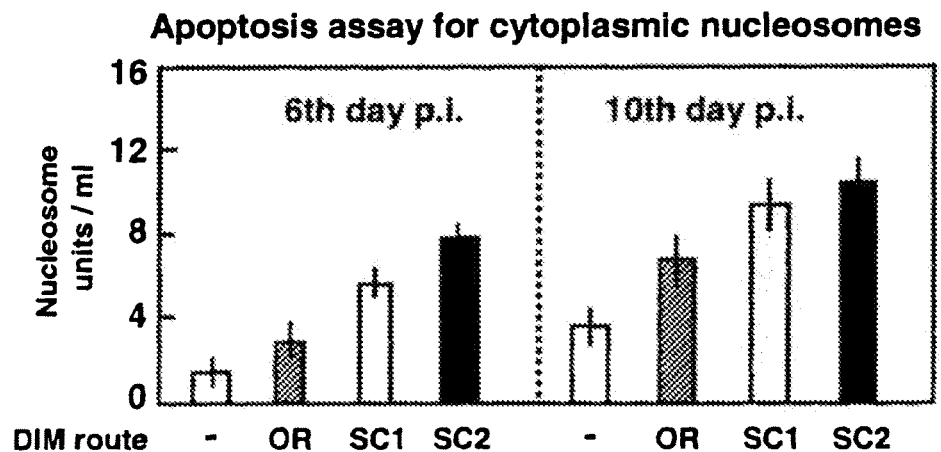

FIGS. 5A-B. DIM stimulates more active apoptosis in RSV-infected mouse lung tissue. Both oral and subcutaneous DIM treatments induced significantly elevated rates of intrapulmonary apoptosis in RSV infected mice. Similar results were seen using 2 different assays for rates of apoptosis: (a) DIM induced increases in apoptosis in mouse lung homogenate as indicated by increased levels of apoptosis-specific, activated Caspase 3; (b) DIM induced increases in apoptosis in mouse lung as indicated by the increased presence of apoptosis-specific nucleosomes. "OR"—orally treated DIM group (250 mg/kg/day from absorption enhanced DIM); "SC1"—1 Low dose parenteral DIM group (15 mg/kg/day), injected SC once daily with DIM suspension; "SC2"—high dose DIM Group (150 mg/kg/day), injected SC once daily with DIM suspension.

Figure 6:
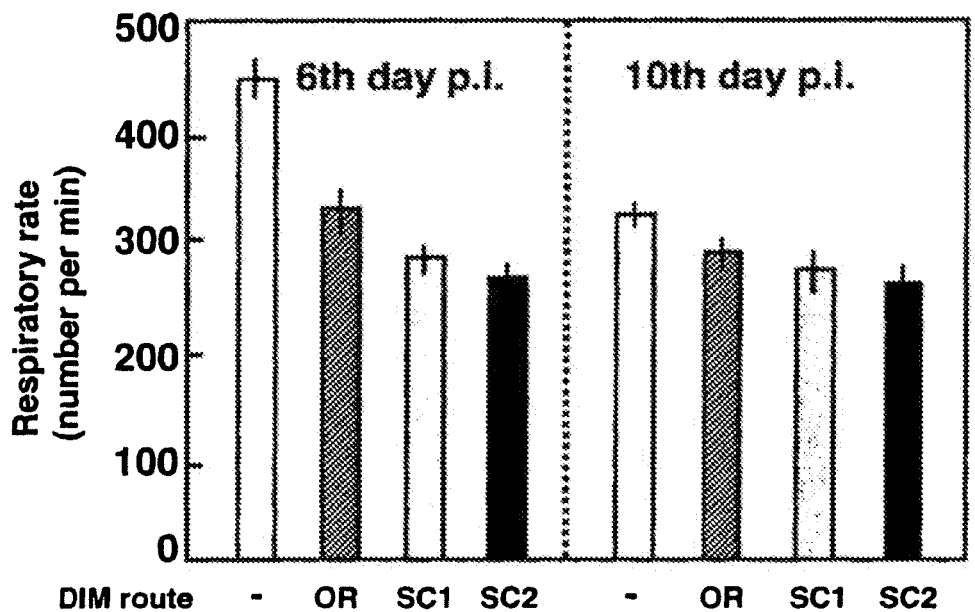

FIG. 6. DIM relieves clinical symptoms in mice. Oral and subcutaneous (SC) treatment with DIM resulted in a normalized respiratory rate in RSV infected mice. DIM-treated mice (oral [OR], SC low dose [SC1], and SC high dose [SC2]), showed a lower respiratory rate at 6 and 10 days post infection (pi), compared to RSV-infected, untreated, control mice (−).

Figure 7:
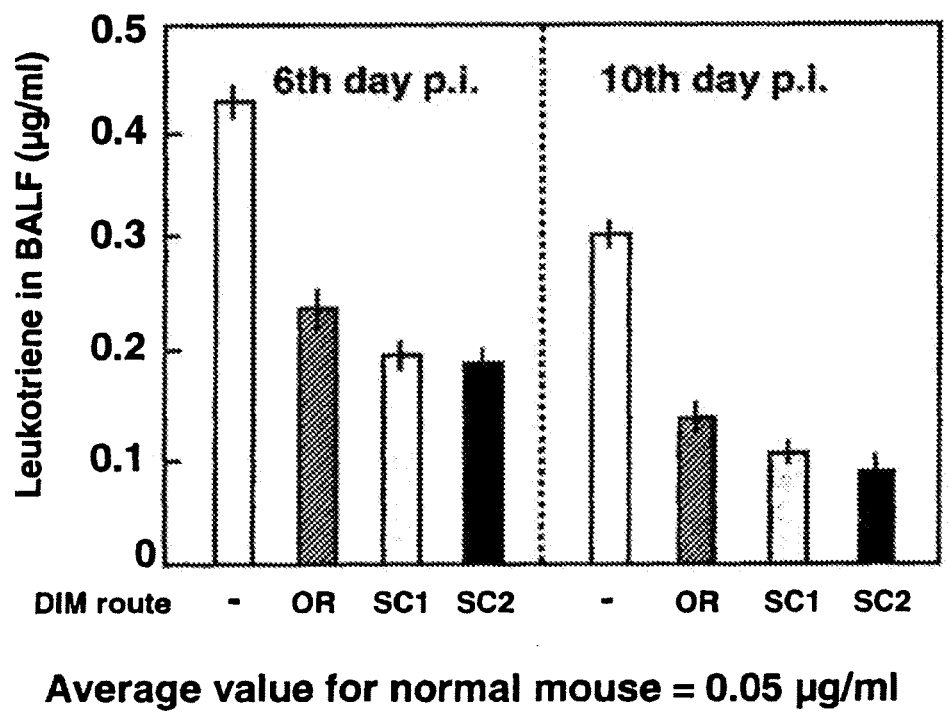

FIG. 7. DIM reduces RSV-related pulmonary inflammation in mice. In RSV-infected mice, oral (OR) and subcutaneous (SC) treatment with DIM resulted in significantly lower levels of lung inflammation associated leukotrienes compared to RSV-infected, untreated control mice (−). Leukotrienes were measured in broncho-alveolar lung fluid (BALF) obtained at necropsy. Reduced BALF leukotrienes relate to diminished bronchospasm in vivo. As presented for both 6 and 10 days post infection (pi), significantly reduced levels of pulmonary leukotrienes were found in DIM-treated RSV-infected mice (oral [OR], SC low dose [SC1], SC high dose [SC2]), compared to control, RSV-infected, untreated mice (−).

5. DETAILED DESCRIPTION OF THE INVENTION

The invention concerns methods and compositions for preventing and treating Respiratory Syncytial Virus (RSV) infections utilizing DIM and DIM-related indoles. The invention further provides methods and compositions for treating RSV infections directed at promoting programmed cell death (apoptosis) of RSV infected cells. In a particular embodiment, combinations of DIM, or a DIM-related indole, and an EGFR inhibitor are provided. The methods and compositions provide improved treatment for RSV-associated infections. The methods and compositions of the invention are also applicable for the treatment and prevention of infections of other paramyxoviridae viruses, particularly in the pneumovirinae subfamily, more particularly in the genus *Metapneumovirus*, involved in diseases in humans and animals including, but not limited to, avian pneumovirus and human metapneumovirus. See Easton et al., 2004, Clinical Microbiology Rev. 17:390-412.

Without being bound by any theory, the methods and compositions of the invention are believed to diminish overactive cellular kinases, and inhibit cell survival signaling pathways downstream of HER receptors, where such overactivity is a response to RSV infection. RSV infection of cells initiates cell-growth and cell-survival mechanisms uniquely attributed to the action of RSV-specific proteins. One of the primary abnormalities in cellular activity is a change in expression and activity of the membrane bound Growth Factor Receptors (GFR) family of signaling proteins (Monick et al., 2005, J. Biol. Chem. 280(3):2147-58). In certain embodiments, the present invention provides therapy for RSV-associated pulmonary disease, including bronchiolitis and pneumonia. Treatment is also provided for other RSV-associated diseases such as pharyngitis, croup, otitis media and conjunctivitis. Treatment, according to the present invention, is believed to diminish persistant, chronic wheezing, asthma, and nasal allergies which often follow RSV infection. In further embodiments, the present invention provides new prophylactic treatments to prevent RSV in high-risk, immunocompromised subjects. Finally, the present infection provides for the treatment and prevention of bovine Respiratory Syncytial Virus (bSRV) infection which is often seen in calves, stressed by colostrum deficiency and cramped housing and transport.

Upon contact with epithelial cells, RSV provides an activation signal for cell survival through the PI3K-Akt kinases which inhibit cellular apoptosis. Specific oncoproteins from RSV promote phosphorylated Akt and inhibit apoptosis. Normally, activation of Akt occurs through occupation of cell surface EGFRs. Principal EGFRs include the Epidermal Growth Factor Receptor (EGFR [HER1]) and related receptors in the HER family of receptors (HER2-4). In RSV-associated conditions, the presence of viral oncoproteins within cells may promote aberrant activation of EGFRs through interaction with the internal domain of the EGFR protein projecting within the plasma membrane, making EGFR activation independent from stimulation of growth factors acting external to the cell. This results in replication of viral DNA within cells with release of mature viral particles further infecting surrounding cells (active infection).

Without being bound by any theory, the present invention employs DIM-related indoles and, optionally, EGFR inhibitors, to inhibit the RSV-associated activation of PI3K-Akt and MAPK and selectively induce apoptosis in actively infected cells, thereby reducing production of mature virus, reducing viral load, and resolving or shortening the period of infection. Prophylactic uses of DIM-related indoles alone or with EGFR inhibitors can prevent primary infection or re-infection with RSV. Selective inhibition of overactive survival and growth signals in RSV-infected cells in the present invention can provide effective therapy, causing virally altered cells to be eliminated by triggering programmed cell death (apoptosis). Timely promotion of apoptosis is RSV infections can limit the extent, duration, and sequelae of RSV-associated disease.

The invention is based in part on expected synergism in using particular combinations of DIM-related indoles and EGFR inhibitors in apoptosis promoting activity in RSV infected cells. Combined use is expected to permit lower dose use of EGFR inhibitors, reducing dose-related side effects of these drugs. In certain embodiments, the compositions of the invention can be used with differentiation promoting agents such as Vitamin-D derivatives (calcitriol[1-alpha-25-dihydroxycholecalciferol]), retinoid derivatives (Vitamin-A, isotretinoin, retinoids), macrophage stimulators, and macrophage colony stimulating factors (Filgrastim and Sargramostim). The combination of a DIM-related indole and an EGFR inhibitor is believed to induce promotion of apoptosis resulting in the selective elimination of infected cells, and cause resolution of RSV-related lesions of epithelial surfaces, and epithelial glands.

5.1 Diindolylmethane-Related Indoles

The DIM-related indoles or DIM compounds useful in the methods and compositions of the invention include DIM (3,3'-diindolylmethane) and the related linear DIM trimer (2-(indol-3-ylmethyl)-3,3'-diindolylmethane [also written: 2 (Indol-3-ylmethyl)-indol-3-yl]indol-3-ylmethane] (LTR). As used herein, "DIM-related compound", "DIM-related indole", and "DIM derivative" are used interchangeably, and refer to both natural metabolites and analogs of DIM, and also to "structurally-related, synthetically-derived, substituted diindolylmethane compounds" and "synthetic derivatives of DIM", such as those disclosed herein and known in the art. As used herein, "cruciferous-related indoles" encompasses the terms "DIM-related compound", "DIM-related indole", and "DIM derivative". One of ordinary skill in the art will recognize that in any of the pharmaceutical compositions or methods of the invention where DIM is used, a DIM-related compound, including a structurally-related, synthetically-derived, substituted diindolylmethane compound or synthetic derivative of DIM, can be used.

The chemical structure of a DIM is as follows (where each of the R groups is H):

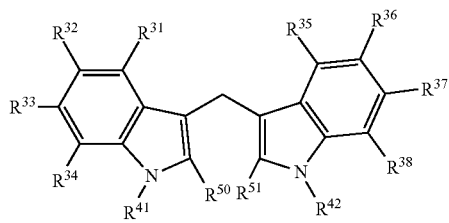

(I)

The chemical structure of LTR is as follows (where each of the R groups is H):

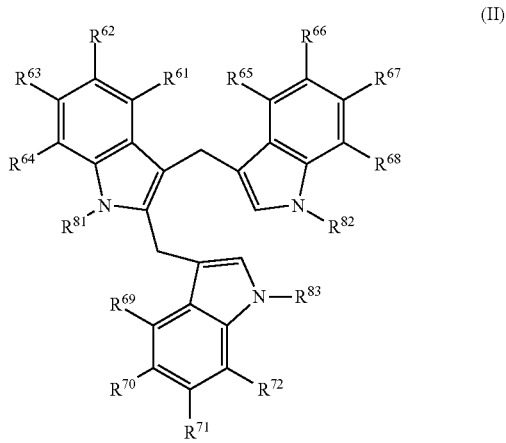

(II)

In certain embodiments, an active hydroxylated or methyoxylated metabolite of DIM, i.e., a compound of formula I, wherein $R^{32}$, $R^{33}$, $R^{36}$, and $R^{37}$ are substituents independently selected from the group consisting of hydrogen, hydroxyl, and methoxy, and $R^{31}$, $R^{34}$, $R^{35}$, $R^{38}$, $R^{41}$, $R^{42}$, $R^{50}$, and $R^{51}$ are hydrogen, is utilized.

In certain embodiments, an active hydroxylated or methyoxylated metabolite of LTR, i.e., a compound of formula II, wherein $R^{62}$, $R^{63}$, $R^{66}$, $R^{67}$, $R^{70}$, and $R_{71}$ are substituents independently selected from the group consisting of hydrogen, hydroxyl, and methoxy, and $R^{61}$, $R^{64}$, $R^{65}$, $R^{68}$, $R^{69}$, $R^{72}$, $R^{81}$, $R^{82}$, and $R^{83}$ are hydrogen, is utilized.

In an alternative embodiment, active DIM derivatives with $R_{32}$ and $R_{36}$ substituents made up of ethoxycarbonyl groups, and $R_{50}$, $R_{51}$ are either hydrogen or methyl, are utilized. In another embodiment, active substituted DIM derivatives including methylated and chlorinated compounds, exemplified by those that include 5,5'-dimethylDIM (5-Me-DIM), 2,2'-dimethylDIM (2-Me-DIM), and 5,5'-dichloroDIM (5-Cl-DIM) are described in U.S. Patent Application Publication No. 20020115708 by Safe, published Aug. 22, 2002, incorporated herein by reference in its entirety, are utilized in the present invention. In another embodiment, active DIM derivatives include imidazolelyl-3,3'-diindolylmethane, including nitro substituted imidazolelyl-3,3'-diindolylmethanes, and additional DIM-related compounds described in U.S. Patent Application Publication No. 2004/0043965 by Jong, Ling, published Mar. 4, 2004, incorporated herein by reference in its entirety, are utilized.

In certain embodiments, a DIM related compound has formula (III):

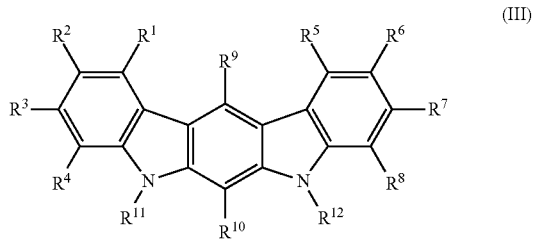

(III)

wherein:
$R^1$, $R^2$, $R^3$, $R^4$, $R^5$, $R^6$, $R^7$, $R^8$, $R^9$, and $R^{10}$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms; and $R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl, with the provisos that: at least one of $R^1$, $R^2$, $R^3$, $R^4$, $R^5$, $R^6$, $R^7$, $R^8$, $R^9$, $R^{10}$, $R^{11}$ and $R^{12}$ is other than hydrogen; and when $R^1$, $R^2$, $R^3$, $R^4$, $R^5$, $R^6$, $R^7$, and $R^8$ are selected from hydrogen, halo, alkyl and alkoxy, then $R^{11}$ and $R^{12}$ are other than hydrogen and alkyl.

A preferred embodiment includes the use of 2,10-dicarbethoxy-6-methoxy-5,7-dihydro-indolo-[2,3-b]carbazole (SRI13668 (SRI Inc., Menlo Park, Calif.)). Additional preferred embodiments include the use of 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole (SRI Inc., Menlo Park, Calif.).

In another embodiment, a DIM related compound has formula (IV):

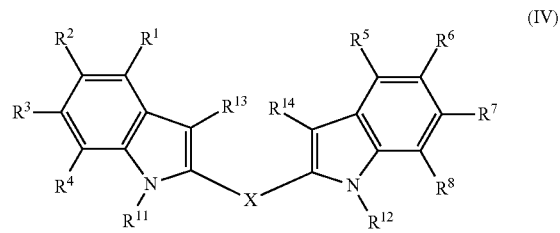

(IV)

wherein:

$R^1$, $R^2$, $R^3$, $R^4$, $R^5$, $R^6$, $R^7$, and $R^8$ are substituents independently selected from the group consisting of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_5$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, phosphino, and combinations thereof, and further wherein any two adjacent (ortho) substituents may be linked to form a cyclic structure selected from five-membered rings, six-membered rings, and fused five-membered and/or six-membered rings, wherein the cyclic structure is aromatic, alicyclic, heteroaromatic, or heteroalicyclic, and has zero to 4 non-hydrogen substituents and zero to 3 heteroatoms, with the proviso that one but not both of $R^2$ and $R^6$ is amino, mono-substituted amino, or di-substituted amino;

$R^{11}$ and $R^{12}$ are independently selected from the group consisting of hydrogen, $C_1$-$C_{24}$ alkyl, $C_2$-$C_{24}$ alkoxycarbonyl, amino-substituted $C_1$-$C_{24}$ alkyl, ($C_1$-$C_{24}$ alkylamino)-substituted $C_1$-$C_{24}$ alkyl, and di-($C_1$-$C_{24}$ alkyl)amino-substituted $C_1$-$C_{24}$ alkyl;

$R^{13}$ and $R^{14}$ are defined as for $R^1$, $R^2$, $R^3$, $R^4$, $R^5$, $R^6$, $R^7$, and $R^8$, with the proviso that at least one of $R^{13}$ and $R^{14}$ is other than hydrogen; and X is O, S, arylene, heteroarylene, $CR^{15}R^{16}$ or $NR^{17}$ wherein $R^{15}$ and $R^{16}$ are hydrogen, $C_1$-$C_6$ alkyl, or together form $=CR^{18}R^{19}$ where $R^{18}$ and $R^{19}$ are hydrogen or $C_1$-$C_6$ alkyl, and $R^{17}$ is as defined for $R^{11}$ and $R^{12}$.

A preferred embodiment includes the use of 2,6-dicarbethoxy-3,3'-dimethyl-13,14-diindolylmethane (SRI Inc., Menlo Park, Calif.).

In another embodiment, a DIM related compounds has formula (V):

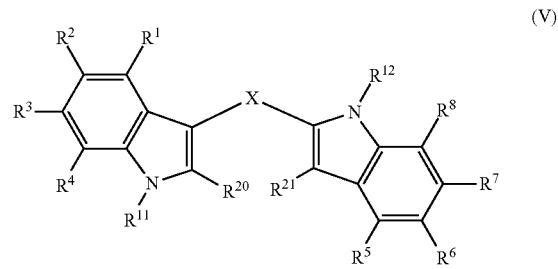

(V)

wherein:

$R^1$, $R^2$, $R^3$, $R^4$, $R^5$, $R^6$, $R^7$, $R^8$, $R^{11}$, $R^{12}$, and X are defined as for compounds of formula (III); and $R^{20}$ and $R^{21}$ are defined as for $R^1$, $R^2$, $R^3$, $R^4$, $R^5$, $R^6$, $R^7$, and $R^8$.

In yet another embodiment, the DIM-related indole is an indole-3-carbinol tetrameric derivative (Brandi et al., 2003, Cancer Res. 63:4028-4036).

5.2 Growth Factor Receptor Inhibitors

The EGFR inhibitors of use in the present invention include, but are not limited to, small molecule drugs which inhibit one or more EGFRs, monoclonal antibodies inactivating EGFRs, and antisense DNA or RNA inactivating EGFR DNA or RNA delivered to a cell using gene therapy. EGFRs which may be inhibited include any EGFR known in the art. See, e.g., Rajkumar, 2001, Current Science 81:535-541.

Small molecular EGFR inhibitors suitable for use in the invention include the EGFR inhibitors, Gefitinib (N-(3-chloro-4-fluorophenyl)-7-methoxy-6-(3-morpholinopropoxy)quinazolin-4-amine, Iressa®, AstraZeneca, UK) and related compounds (see European Patent Application No. 0566226; International Patent Applications WO 96/33980 and WO 97/30034; Woodburn et al., 1997, Proc. Amer. Assoc. Cancer Research 38:633; and Woodburn et al., 1999, Pharmacol. Ther. 82, 241-250), Erlotinib (N-(3-ethynylphenyl)-6,7-bis(2-methoxyethoxy)quinazolin-4-yl]-(3-ethynylphenyl)amine, Tarceva®, OSI Pharmaceuticals) and related compounds (see International Patent Applications WO 96/30347 and WO 99/55683), CI 1033 (6-acrylamido-N-(3-chloro-4-fluorophenyl)-7-(3-morpholinopropoxy)quinazolin-4-amine, Pfizer) and related compounds (see International Patent Applications WO 97/38983 and WO 00/31048, and Smaill et al., J. Med. Chem., 1999, 42:1803-1815), PKI 166 (4-[(1R)-1-phenylethylamino]-6-(4-hydroxyphenyl)-7H-pyrrolo[2,3-d-]pyrimidine, Novartis Pharma, AG [Basel]) and related compounds (see International Patent Application WO 97/02266).

Other examples of EGFR inhibitors include, but are not limited to, resveratrol (Stewart et al., 2004, Invest. New Drugs 22:107-117) and epigallocatechin-3-gallate (Sah et al., 2004, J. Biol. Chem. 279:12755-12762).

The specific EGFRs to be inhibited relate to those overactivating the PKB/Akt signaling pathway and include the HER family of EGFRs, PDGFR, and VEGFR. Representative specific small molecule drugs useful in the present invention, presented in relation to the EGFR inhibited are summarized in Table 1.

Representative specific EGFR inhibiting monoclonal antibodies useful in the present invention presented in relation to the EGFR inhibited, include those that appear in Table 2.

TABLE 2

| Drug | Manufacturer | Class | HER | VEEGFR | PDGF |
|---|---|---|---|---|---|
| Cetuximab (Erbitux) | ImClone/ B-MS | Mouse/ human mAb | X | | |
| Trastuzumab Herceptin | Genentech | mAb | X | | |
| MDX-210 | Medarex | mAb | X | | |
| ABX-EGF | Abgenix/ Immunex | mAb | X | | |
| TheraCIM | YM | mAb | EGFR | | |
| Panitumumab | AbBenix | mAb | EGFR | | |
| EMD-72000 | Merck | mAb | EGFR | | |
| bevacizumab (Avastin) | Genentech/ Hoffman | mAb | | X | |
| Ranibizumab (Lucentis) | Genentech/ Novartis | mAb | | X | |

5.3 Optional Additional Agents

A number of additional agents can optionally be used in the methods and compositions of the invention with DIM, or a DIM-related indole, with or without an EGFR inhibitor. Representative agents include, but are not limited to, differentiation promoting agents, farnesyl transferase inhibitors, proteo-

TABLE 1

Orally active, GRF Inhibitor Drugs for Use with DIM-Related Indoles:

| | | | HER | | | | | |
|---|---|---|---|---|---|---|---|---|
| | | | EGFR | | | | | |
| Drug | Manufacturer | Drug Class | I | II | IV | IV | VEGFR | PDGF |
| ZD1839 Gefitinib (Iressa) | AstraZeneca | Small Head Group Quinazoline (reversible) | X | | | | | |
| ZD6474 | AstraZeneca | | X | X | | | | |
| OSI-774 Erlotinib (Tarceva) | OSI//Roche/ Genentech | Small Head Group Quinazoline (reversible) | X | | | | | |
| Lapatinib GW-572016 | GlaxoSmithKline | Large Head Group Quinazoline | X | X | | | | |
| GW-2016 | GlaxoSmithKline | | X | X | | | | |
| STI-571 Imatinib Myesylate (Gleevec) | Novartis | | X | | | | | X |
| EKB-569 | Wyeth | (irreversible) | X | X | | | | |
| CI-1033 (PD183805) Cancertinib | Pfizer | 4-anilinoquinazoline (irreversible) | X | X | X | X | | |
| SU5416 Semaxanib | Sugen Pharma/Pfizer | indolin-2-ketone | | | | | X | |
| SU11248 | Sugen Pharma/Pfizer | indolin-2-one | | | | | X | X |
| SU6669 | Sugen Pharma | | X | | | | | |
| Vatalanib PTK787 (ZK222584) | Novartis/Schering | anilino- phthalazines | X | X | X | X | X | X |
| PKI-166 | Novartis | Pyrrolopyrimidines (reversible) | X | X | | | X | |
| CEP-7055 | Sanofi-Synthelab | Dimethylglycene | | | X | X | | | some inhibitors, RAF inhibitors, RSV anti-viral drugs, immune stimulating mushroom extracts, endoplasmic reticulum stress inducers, and resveratrol. The additional agents are believed to support more active apoptosis in virally infected cells and more efficient presentation of viral-specific antigens to the host immune system through activated macrophage function.

Differentiation promoting agents useful in the present invention include, but are not limited to, Vitamin D3, calcitriol (Rocaltrol, Roche Labs, Nutley, N.J.), Vitamin A, a retinoid derivative, such as isotretinoin (Acutane, Roche Labs, Nutley, N.J.), macrophage stimulators, biotin (Vitamin H, Product A14207, Alpha Aezar, Ward Hill, Mass.) and granulocyte-macrophage colony stimulating factors such as sargramostin (Leukine, Berlex Labs). Useful macrophage stimulators include, but are not limited to, beta-glucans, and extracts of the root of North American ginseng (*Panax quinquefolium*) containing poly-furanosyl-pyranosyl-saccharides (CV Technologies Inc., Edmonton). Useful *Panax quinquefolium* extracts are described in U.S. Pat. No. 6,083,932 by Pang et al. which is herein incorporated by reference in its entirety. Beta-glucans include those derived from *Saccharomyces cerevisiae* (En-Bio Technology Co., Ltd.). Other useful fungal extracts containing branched glucans are derived from mushrooms, such as the maitake mushroom (*Grifola frondosa*). Oral use of beta-glucans in viral disease has been described (Jung et al., 2004, J Vet Med B Infect Dis Vet Public Health. 51(2):72-6).

RSV anti-viral drugs include, but are not limited to, selected RSV-vaccine, anti-RSV immunoglobulin, hAnti F-glycoprotein, anti-RSV monoclonal antibody, plant flavinoid, benzoditin, ribavirin, ganciclovir, valganciclovir, cidofovir, and phosphocarnet.

Agents which increase endoplasmic reticulum stress, i.e., endoplasmic reticulum stress inducers, complement the pro-apototic activity of DIM-related indoles. Prefered endoplasmic reticulum stress inducers have low toxicity and include biotin (Vitamin H) and selenium, provided as bioavailable selenomethionine, sodium selenite, methylselenocysteine. More preferred is methyl-seleninic acid (Smith et al., 2004, Anticancer Res. 24(3a):1401-8).

Inhibition of proteosome function indirectly causes endoplasmic reticulum stress, making the use of Bortezomib, a proteosome inhibitor, useful in combination with DIM-related indoles of the present invention.

5.4 Prevention and Treatment of Respiratory Syncytial Virus (RSV) Associated Conditions The present invention provides for the prevention and therapy of RSV associated conditions which include infections and post-infectious chronic inflammatory conditions. Currently, this spectrum of RSV-associated conditions lacks adequate and effective therapy due to failure of previous approaches to selectively eliminate RSV-altered cells and target the anti-apoptotic cell signaling pathways activated by RSV and its virus specific proteins. RSV-associated conditions include upper and lower airway infections, and are present in greater prevalence in newborns, infancy, and childhood. Characteristic RSV infectious symptoms include bronchiolitis (wheezy bronchitis), asthma (expiratory wheezing), and respiratory distress with coughing (pneumonia). RSV associated conditions characteristic of children include conjunctivitis, persistent rhinorrea, nasal congestion pharyngitis and cough. Pneumonia is the most common manifestation of RSV in the elderly.

5.4.1 Methods of Prophylaxis

Protecting against a primary RSV infection in a seronegative individual or protecting against re-infection with RSV following seroconversion with loss of adequate protective antibody levels involves the preemptive or chemopreventive use of DIM-related indoles, typically without an EGFR inhibitor. Typically, DIM-related indoles are used for chemoprevention in immunocompromised individuals with acquired HIV infection or AIDS, inherited immune dysfunction, or drug induced immune dysfunction following organ transplantation, before or after bone marrow engraftment, following treatment of autoimmune disease, or following chemo/radiation treatment of cancer. The use of a EGFR inhibitor in these patient populations would generally not be worth the risk of side effects associated with EGFR inhibitors. Suppression of immune function results in much greater risk for a severe life-threatening RSV infection. In healthy individuals, anti-RSV cytotoxic T-cells and antibody producing B-cells continually attack RSV infected cells that are producing virus. This controls and resolves infection and limits RSV from spread from the upper to the lower respiratory tract. By using DIM prophylactically, apoptosis would be promoted in RSV-infected cells as soon as active viral replication began as characterized by increased activity of PI3K and Akt. Apoptosis of virally infected cells enhances presentation of viral antigenic proteins supporting the host immune system. Therefore, in certain embodiments, DIM can be used with prophylactic RSV vaccines.

Alternatively, DIM is used for RSV prophylaxis in conjunction with differentiation enhancing agents like Vitamin-D, Vitamin-A, biotin (Vitamin H), macrophage stimulators, and macrophage colony stimulators which stimulate the final differentiation of respiratory epithelia and of monocytes into macrophages. Useful macrophage stimulators include, but are not limited to, beta glucans, including those derived from *Saccharomyces cerevisiae* (En-Bio Technology Co., Ltd.), and extracts of the root of North American ginseng (*Panax quinquefolium*) containing poly-furanosyl-pyranosyl-saccharides (CV Technologies Inc., Edmonton). Macrophages contribute to the complete resolution of RSV-associated epithelial damage.

Used prophylactically during seasons of increased RSV activity, DIM-related indoles are provided in adequate dose in oral formulations to at risk infants, children, and adults. In cattle, DIM-related indoles are used propylactially orally or parenterally in calves when there is evidence of RSV infection in the herd and during transport.

5.4.2 Active Infections

Active RSV-associated infections include Upper Respiratory Infections (URI's), Pharyngitis, Bronchitis, Bronchiolitis, Pneumonia, Otitis Media, and Conjunctivitis. The presence of RSV in nasal or pulmonary secretions results in transmission between individuals by droplet, aerosol, or direct contact. In immunocompromised individuals, the methods of the present invention provide for treatment of RSV associated bronchiolitis and pneumonia. Treatment of the above conditions utilize DIM-related indoles administered alone or in combination with currently available RSV anti-viral drugs which include ribavirin, RSV-IG, and/or Palivizumab. The use of a combination of a DIM-related indole and a EGFR inhibitor is generally not warranted in these cases, but may be used in severe cases. For example, in hospitalized patients requiring tracheal intubation and ventilator support for RSV-associated pulmonary failure, combined therapy with DIM, or DIM-related indole, and EGFR inhibitor is indicated. In this setting, DIM is best administered intravenously and/or via aerosol at the maximal tolerated dose (MTD). The EGFR inhibitor is generally administered intravenously, orally, and/or by aerosol, at the average tolerated dose (ATD). Combined therapy is continued at a lower dose for each agent following resumption of un-assisted breathing and symptomatic improvement.

5.4.3 Sequella to Active Infections

The therapeutic use of DIM, or a DIM-related indole, and an EGFR inhibitor is further utilized as chronic therapy following RSV-associated pulmonary disease to prevent postinfection brochospastic cough, wheezing, asthma, chronic sinusitis, and general atopy. RSV infection is known to contribute to chronic immune dysregulation, asthma, nasal allergies, and other chronic inflammatory disorders through mechanisms that involve activation of NFkappaB and Interleukin-8 (IL-8) (Fiedler et al., 1996, J Virol. 70:9079-82). Elevation of IL-8, IL-9, and pulmonary leukotrienes together with activation of NF-kappaB are known to accompany both active RSV-infection and asthma (Vignola et al., 2001, J Allergy Clin Immunol. 108:738-46). Therefore, in one embodiment, chronic oral use of DIM is utilized following RSV infection in children to diminish subsequent devolpment of wheezing, asthma, or other immunopathology. Typically, DIM formulated for enhanced absorption is taken orally at the ATD. In severe post RSV asthma, oral EGFR inhibitors can be utilized intermittently at their minimal effective dose (MED). Chronic elevation of IL-8 as also been noted in cases of non-small cell lung cancer (McKeown et al., 2004, Br J Cancer. 91:1993-5).

5.5 Prevention and Treatment Parameters Using a DIM-Related Indole or Combined Use of DIM-Related Indoles and EGFRs The invention provides for three (3) categories of treatment using DIM-related indoles and DIM-related indoles with EGFR inhibitors: (I) chemoprevention of primary or secondary RSV infection with DIM-related indoles; (II) treatment of active RSV infections with DIM-related indoles, with or without EGFR inhibitors, and established RSV anti-viral drugs; and (III) treatment of RSV-related persistant pulmonary and allergic symptoms with DIM-related indoles, bronchodilators, and anti-inflammatory agents such as salicylates and COX-2 inhibitors. In category II, treatment includes the combination of DIM-related indole and EGFR inhibitors with or without additional modalities of treatment, including, but not limited to, intravenous or intramuscular administration of anti-RSV antibodies (e.g., RespiGam [RSV-IVIG, MedImmune] and Synagis [Palivizumab, MedImmune]).

Based on the category of treatment, in embodiments using a combination of a DIM-related indole and a EGFR inhibitor, the DIM-related indole and EGFR inhibitor can be used in 3 defined dose ranges. These dose ranges include Minimal Effective Dose (MED), Average Tolerated Dose (ATD), and Maximal Tolerated Dose (MTD). The MED relates to the lowest dosage range where biologic and metabolic effects from DIM-related indoles and EGFR inhibitors are seen. The ATD is the dose range higher than the MED where consistent biologic effects are seen, but where side effects are rare. The MTD is the dose range higher than the ATD where side effects are often seen but are tolerable during the treatment protocol. In embodiments where DIM is administered without an EGFR inhibitor, the same defined dose ranges may be used.

The following are general descriptions of DIM-related indole and combined DIM-related indole and EGFR inhibitor therapy according to category of treatment.

I. Chemoprevention of Primary and Secondary RSV Infections, Including Prophylactic Uses DIM-related indoles, with or without RSV anti-viral agents, can be used to prevent primary or secondary RSV infection in individuals who are at risk of infection or re-infection with RSV. This applies to prospective solid-organ transplant recipients, immunosupressed bone marrow graft recipients, and infants born prematurely. It also applies to pregnant women who are seronegative for RSV during pregnancy. Treatment with DIM-related indoles is also used by seropositive individuals wishing to prevent re-infection with RSV who have pre-existing conditions including, but not limited to, HIV infection, AIDS, or other acquired immunodeficiency.

Prophylactic treatment of RSV infections and RSV-related chronic conditions with DIM and resveratrol is also provided. The combination of a DIM-related indole and resveratrol can be used by at risk children or adults to reduce and prevent spread of RSV from previously exposed individuals to un-exposed individuals. Typically a daily oral dose of 50-250 mg/day (1-3 mg/kg/day) of DIM-related indole in a suitable formulation is taken along with a daily oral dose of 25-1000 mg (0.5-10 mg/kg/day) of reseveratrol or resveratrol-related stillbene in a suitable formulation.

In another embodiment, prophylactic treatment of RSV infections and RSV-related chronic conditions with DIM and one or more differentiation enhancing vitamins, such as vitamin D and/or biotin, is provided. The combination of a DIM-related indole and a differentiation enhancing vitamin can be used by at risk children or adults to reduce and prevent the spread of RSV from previously exposed individuals to un-exposed individuals. Typically a daily oral dose of 50-250 mg/day (1-3 mg/kg/day) of a DIM-related indole in a suitable formulation is taken along with a daily oral dose of 200-10,000 Internatioal Units (IU's) of Vitamin D, for example, taken as vitamin $D_2$ (ergocalciferol) or vitamin $D_3$ (cholecalciferol). Biotin (Vitamin H) is generally taken in oral doses of 0.1-20 mg/day in conjunction with DIM-related indole.

In yet another embodiment, prophylactic treatment of RSV infections and RSV-related chronic conditions with DIM and macrophage stimulating extracts of the root of North American ginseng (*Panax quinquefolium*) containing poly-furanosyl-pyranosyl-saccharides is provided. The combination of a DIM-related indole and *Panax quinquefolium* extract can be used by at risk children or adults to reduce and prevent spread of RSV from previously exposed individuals to un-exposed individuals. Typically a daily oral dose of 50-250 mg/day (1-3 mg/kg/day) of DIM-related indole in a suitable formulation is taken along with a daily oral dose of 400-1,800 mg/day (6-30 mg/kg/day) of *Panax quinquefolium* extract in a suitable formulation (CV Technologies Inc., Edmonton). Alternatively, beta-glucans including those derived from *Saccharomyces cerevisiae* (En-Bio Technology Co., Ltd.), can be used in place of *Panax quinquefalium* extracts as macrophage stimulators. Oral use of beta-glucans in viral disease has been described (Jung et al., 2004, J Vet Med B Infect Dis Vet Public Health. 51(2):72-6). Typically, beta-glucans are administered orally using a dose of 10-100 mg/kg/day in conjunction with DIM-related indoles.

II. Therapy of Active RSV Infections

Active RSV infections, as exemplified by coryza, pharyngitis, cough, dypsnea, and tacypnea, with or without fever, are treated with DIM-related indoles or a combination of a DIM-related indole and a EGFR inhibitor. Combined DIM-related indole/EGFR inhibitor therapy can be used with standard RSV anti-viral drugs such as ribavirin in cases of underlying immunodeficiency. The uses of the antiviral drugs are well known and specified in De Clerq (2004, J of Clinical Virology 30:115-133). In a preferred embodiment, DIM-related indoles and EGFR inhibitors are used at the highest tolerated doses in severe RSV infections in hospitalized patients. In sick infants or toddlers not requiring hospitalization, twice daily oral dosage of DIM at the MTD in an oral suspension is preferred.

For life threatening conditions, intravenous DIM-related indoles would be administered with or without additional aerosolized DIM. As the clinical condition requires, an appropriate EGFR inhibitor is further utilized together with optional intravenous or intramuscular administration of one of more of the following: anti-RSV antibodies (e.g., Respi-Gam [RSV-IVIG, MedImmune] and Synagis [Palivizumab, MedImmune]), a farnesyl transferase inhibitor, a proteosome inhibitor, a RAF inhibitor, an RSV-vaccine, anti-RSV immunoglobulin, hAnti F-glycoprotein, anti-RSV monoclonal antibody, plant flavinoid (PROVIR), benzoditin, ribavirin, ganciclovir, valganciclovir, cidofovir, or phosphocarnet.

In other embodiments, a DIM-related indole is used in combination with resveratrol. For example, a daily oral dose of 150-500 mg/day of DIM-related indole in suitable formulation is taken along with a daily oral dose of 25-1000 mg of resveratrol or resveratrol-related stillbene in a suitable formulation are utilized in adults. In infants and children, a daily oral dose of 2-10 mg/kg/day of DIM-related indole in suitable formulation is taken along with a daily oral dose of 0.5-10 mg/kg/day of resveratrol or resveratrol-related stillbene in a suitable formulation. Alternatively, the DIM-related indole and optionally resveratrol, can be used in combination with a EGFR inhibitor. Typically, Gefitinib at 25-350 mg/day is added in serious cases in adults. Gefitinib at 0.25-5 mg/kg/day is added in serious cases in infants and children. Following clinical improvement, the DIM-related indole, with or without resveratrol, is continued with the Gefitinib lower in its dose range. With stable clinical improvement the DIM-related indole, with or without Resveratrol, is continued.

III. Therapy of RSV-Associated Post-Infectious Sequella

DIM, or a DIM-related indole, and EGFR inhibitors of the present invention are utilized therapeutically following RSV-associated pulmonary disease to treat and prevent post-RSV chronic cough, wheezing, asthma, and nasal allergies. Chronic oral use of DIM is initiated following RSV infection in children to diminish subsequent devolpment of wheezing, asthma, and general risk of nasal and skin allergies (atopy). Typically, DIM formulated for enhanced absorption is taken orally at the ATD for 1-6 months following active RSV infection. In severe post-RSV asthma, oral EGFR inhibitors can be utilized intermittently at their minimal effective dose (MED) on a once weekly basis in addition to daily oral DIM. Besides chronic symptoms and a family history of allergic disease, increased serum IgE and IL-8 levels post-RSV infection can be used as further indicators for the need for chronic administration of DIM, or DIM-related indole.

A summary of the dose ranges appropriate for combined uses of DIM-related indoles with EGFR inhibitors is presented in Table 3. Specific dose ranges for DIM and representative EGFR inhibitors is presented in Table 4. A summary of the applications for combined use of DIM with EGFR inhibitors, anti-viral agents and monoclonal antibodies is presented in Table 5.

TABLE 3

|  | Treatment Category I | Treatment Category II | Treatment Category III |
|---|---|---|---|
| Agent | Chemo-prevention | Active Infection | Post-RSV Sequellae |
| DIM-related indole | ATD | MTD | ATD |
| EGFR inhibitor | MED | MED/ATD | MED |
| Anti-viral Therapy | (−) | (+/−)* | (+/−) |

*Use specified in De Clercq, 2004, J Clin Virol. 30: 115-33.

TABLE 4

Dose Ranges for Combined uses of DIM-Related Indoles and EGFR Inhibitors

| Drug | Manufacturer | Minimal Effective Dose Range (MED) mg/day | Average Tolerated Dose Range (ATD) mg/day | Maximal Tolerated Dose Range (MTD) mg/day |
|---|---|---|---|---|
| Formulated DIM (BR-DIM) | BioResponse | 25-150 | 150-500 | 500-1000 |
| ZD1839 Gefitinib (Iressa) | AstraZeneca | 25-150 | 150-350 | 350-750 |
| Lapatinib GW-572016 | GlaxoSmithKline | 175-500 | 500-900 | 900-1,800 |
| OSI-774 Erlotinib (Tarceva) | OSI/DNA/Roche | 50-150 | 150-200 | 200-400 |
| Imatinib Myesylate (Gleevec) STI-571 | Novartis | 100-300 | 300-400 | 400-800 |
| CI-1033 | Pfizer | 10-100 | 100-500 | 500-700 |
| Efalizumab Xanelin EKB-569 | | 5-25 | 25-75 | 75-200 |
| PKI-166 | Novartis | 10-50 | 50-100 | 100-900 |
| Semaxanib SU5416 | Sugen Pharma/Pfizer | 10-50 mg/m$^2$ | 50-100 mg/m$^2$ | 100-200 mg/m$^2$ |
| CEP-7055 | Sanofi-Synthelab | 25-100 | 100-400 | 400-1000 |

TABLE 5

Summary of combined uses of DIM-related indoles and
EGFR inhibitor therapy for RSV related diseases:

| | RSV-related Use or Condition | Agent | | | |
|---|---|---|---|---|---|
| | | DIM-related Indole | EGFR Inhibitor | Anti-Viral Agent | Monoclonal Antibody |
| I | Prophylaxis of Infection | (+) | (−) | (−)* | (+/−) |
| II | Active Infection | (+) | (+/−) | (+/−)* | (+/−) |
| III | Post Infectious Sequellae | (+) | (+/−) | (−)* | (−) |

(+) = therapy utilized
(−) = therapy not utilized
(+/−) = therapy optionally utilized
*= optional use of Resveratrol

5.6 Administration and Dosage

In certain embodiments, certain combinations of DIM-related indoles, e.g., DIM, and a EGFR inhibitor in topical delivery systems, parenteral delivery systems, oral delivery systems, and simultaneous delivery by multiple routes is believed to provide therapeutic efficacy more than the additive efficacy of each agent used alone at maximal dose. Therefore, methods involving combined use of a DIM-related indole and a EGFR inhibitor at less than their maximal doses is believed to increase both the safety and efficacy of DIM-related indoles and EGFR inhibitors in RSV-associated conditions.

Improved efficacy would result in a shorter duration of required therapy than with individual agents used alone. Combined use is believed to allow a reduction in dose or concentration of each component in topical formulations. Combined use is believed to improve the long term therapeutic result with a lower rate of recurrence due to persisting virally infected cells. Combined use with lowered dose and duration of use would also minimize toxicity.

In methods involving the oral use of one or more DIM-related indoles, e.g., DIM, and a EGFR inhibitor, the oral delivery of indole is facilitated and accomplished according to formulations and methods described in U.S. Pat. No. 6,086,915, incorporated by reference herein in its entirety.

When combined with RSV antiviral drugs for the treatment of RSV infections, DIM-related indoles and EGFR inhibitors can be added to established protocols. For example, DIM related indoles and EGFR inhibitors can be used in conjunction with gancyclovir and anti-RSV immunoglobulins in prophylaxis and treatment before and after organ transplantation (Bonaros et al., 2004, Transplantation 77:890-7).

The treatment of pulmonary, cutaneous, oral, and pharyngeal manifestations of RSV infection with an oral DIM-related indole, e.g., DIM, is facilitated by topical, intravenous, intra-lesional, and aerosol application of DIM-related indoles in specific relative doses to the simultaneous administration of a EGFR inhibitor. These therapies include production of tinctures, liposomes, creams, or rectal suppositories, eye drops, emulsions for intravenous use, and injectable suspensions to deliver synergistic amounts of these agents. Injectable formulations include cyclodextrin complexed DIM-related indoles and liposome encapsulated DIM-related indoles.

5.7 Pharmaceutical Compositions

Pharmaceutical Dosage Forms for DIM-related indoles: Multi-application DIM-related indole containing particles are manufactured by various techniques including spray drying, spray cooling, selective precipitation, crystallization and other particle forming methods. The resulting particles are used in the manufacture of the following dosage forms, some of which are described in U.S. Pat. No. 6,086,915, incorporated by reference herein in its entirety.

I. Spray Dried Microencapsulated Solid Dispersions
1. TPGS/phosphopholipid spray-dried particles. Production of absorption-enhanced DIM-related indole particle formation is provided in U.S. Pat. No. 6,086,915.
2. Liquid emulsions using TPGS/phosphopholipid spray-dried particles. Production of emulsions for oral use utilizes absorption-enhanced DIM-related indole particle formation as provided in the U.S. Pat. No. 6,086,915.
3. Flavored DIM granules for oral use (Chocolate, Orange "sprinkles"). Production of flavored granules for oral use utilizes absorption-enhanced DIM-related indole particles (DIM/TPGS) as provided in U.S. Pat. No. 6,086,915. Production steps include dry mixing DIM/TPGS particles with maltodextrin granules, addition of flavoring particles and granulation using a standard fluid bed granulator.
4. Flavored suspension of DIM-related indole for pediatric use using taste masking and component particles engineered for enhanced DIM absorption.
5. Dry granules, with or without flavorings, for use as additives to animal feed.

II. Spray Dried Polymer Based Solid Dispersions
Production techniques for DIM-related indoles may utilize those described in U.S. Patent Application No. 20030072801, entitled "Pharmaceutical compositions comprising drug and concentration-enhancing polymers," herein incorporated by reference in its entirety. In particular production involes the following dissolution enhancing polymers, used with and without lipid stabilizers:
1. Polymer included: Hydroxy Propyl Methylcellulose
2. Polymer: Hydroxy Propyl Cellulose III. Cyclodextrin Based Formulations
Examples of manufacturing techniques are described in U.S. Pat. No. 4,877,778 and U.S. Patent Applications No. 20040053888; 20030073665; and 20020068720, each of which is herein incorporated by reference in its entirety. Using cyclodextrin loading production techniques to incorporate DIM-related indoles the following final formulations are produced:
1. Dry particle complex for oral use
2. Intravenous emulsion
3. Parenteral emulsion
4. Aerosol suspension IV. Nanoparticle-Based Dispersions
Examples of manufacturing techniques are described in U.S. Pat. Nos. 6,288,040; 6,165,988; 6,117,454; and U.S. Patent Application Publication No. 20030032601; each of which is incorporated by reference in its entirety. Using nanoparticle production techniques to incorporate DIM-related indoles the following final formulations are produced:
1. Dry particle complex for oral use.
2. Intravenous emulsion
3. Parenteral emulsion
4. Aerosol suspensions V. Liposome Based Formulations
Examples of manufacturing techniques are described in U.S. Pat. Nos. 4,906,476; 5,006,343; and U.S. Patent Application Publication No. 20030108597. Using liposome production techniques to incorporate DIM-related indoles the following final formulations are produced:

1. Dry particle complex for oral use
2. Intravenous emulsion
3. Parenteral emulsion
4. Aerosol suspension VI. Pulmonary Targeted Formulations Pulmonary targeting includes intravenous emulsions which are concentrated in lung tissue and aerosol formulations with or without lipids and RSV-specific antibodies.

1. Phospholipid complexed intravenous emulsions
2. Cyclodextrin-based intravenous emulsions
3. Aerosol suspension of crystalline DIM-related indole
4. Aerosol suspension formed with DIM loaded liposomes
5. Aerosol suspension complexed with Anti-RSV monoclonal antibodies
6. Intravenous suspension complexed with Anti-RSV monoclonal antibodies VII. Leukocyte Targeted Formulations 1. Phospholipid complexed intravenous emulsions
2. Cyclodextrin-based intravenous emulsions
3. Aerosol suspension
4. Intravenous suspension complexed with Anti-RSV monoclonal antibodies
5. Aerosol suspension complexed with Anti-RSV monoclonal antibodies VIII. DIM Tinctures and Suspensions 1. Oral tinctures prepared with ethanol
2. Parenteral tincture prepared with ethanol
3. Microcrystalline suspension for oral use
4. Parenteral microcrystalline suspension
5. Sustained release parenteral suspension
6. Opthalmic suspension
7. Opthalmic emulsion
8. Otic suspension The pharmaceutical compositions according to the present invention preferably comprise one or more pharmaceutically acceptable carriers and the active constituents, e.g., a DIM-related indole with or without an EGFR inhibitor. The carrier(s) must be "acceptable" in the sense of being compatible with the other ingredients of the composition and not deleterious to the recipient thereof.

It will be appreciated that the amounts of DIM or other DIM-related indole and/or a EGFR inhibitor, required for said treatments will vary according to the route of administration, the severity of the RSV-related disease, age, and medical history of the subject, the galenic formulation of the pharmaceutical composition, etc.

Preferably, the DIM used in the invention has been processed to enhance bioavailability, as is described in U.S. Pat. No. 6,086,915, incorporated herein by reference in its entirety; however any suitable preparation of pure diindolylmethane can be used in the methods and compositions of the invention.

In general, a suitable (therapeutically effective) amount of Diindolylmethane is preferably administered in an absorption enhancing formulation, as described in U.S. Pat. No. 6,086,915, at 150-750 mg per day as a suspension of microparticles in a starch carrier matrix. Structurally-related, synthetically-derived, substituted diindolylmethane's, as described by Jong (U.S. Patent Application Publication No. 2004/0043965) are administered according to the present invention in an acceptable formulation for oral administration in a dose of 10-400 mg/day or 10-700 mg/day. Preferably, these substituted diindolylmethanes are administered in an absorption-enhanced formulation at a dose of 50 to 250 mg/day. The actually administered amounts of DIM or a substituted diindolylmethane may be decided by a supervising physician. The DIM-related indole of the invention is preferably administered in combination with an EGFR antagonist administered by either oral, topical, or parenteral routes.

Typically, in the methods and compositions employing an EGFR inhibitor, e.g., Iressa, the EGFR inhibitor would be employed in a dose of 50-500 mg/day, more preferably, 50-250 mg/day, or 50-100 mg/day. Alternatively, a low, effective dose of another EGFR inhibitor such as OSI-774 (Erlotinib, Tarceva), CI 1033 [Parke-Davis Pharmaceutical Research (Ann Arbor, Mich.), PKI 166 [Novartis Pharma, AG (Basel, Switzerland)] or GW2016 would be employed at doses of 25-500 mg/day. As an example of such combined therapy, an absorption-enhanced formulation of DIM in a dose of 300 mg [75 mg actual DIM] is taken orally twice daily along with a dose of 100 mg of Iressa (ZD1839, Gefitinib) taken once daily. Further details of the clinical use of EGFR inhibitors for combined use with DIM and/or DIM-related compounds are described in the following publications, incorporated herein by reference in its entirety (Janmaat et al., 2003, Oncologist 8:576-86; and Janmaat et al., 2003, Drugs Today (Bare) 39 Suppl C:61-80).

Therapeutic formulations include those suitable for parenteral (including intramuscular and intravenous), topical, oral, vaginal, rectal, conjunctival or intradermal administration. Preferred routes of adminstration include aerosol administration, oral administration, intranasal administration, intrapulmonary administration, intravenous administration, intramuscular administration, conjunctival administration, vaginal administration, rectal administration, or topical administration. Oral administration for DIM is the most preferred route. Thus, the pharmaceutical composition may be formulated as tablets, pills, syrups, capsules, suppositories, ophthalmic suspension, flavored oral suspension, granules for use in animal feed, formulations for transdermal application, powders, especially lyophilized powders for reconstitution with a carrier for intravenous administration, etc.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavoring agent, such as peppermint, methyl salicylate, or orange flavoring.

Therapeutic formulations suitable for oral administration, e.g., tablets and pills, may be obtained by compression or molding, optionally with one or more accessory ingredients. Compressed tablets may be prepared by mixing phytochemicals, and compressing this mixture in a suitable apparatus into tablets having a suitable size. Prior to the mixing, the DIM-related indole or EGFR inhibitor may be mixed with a binder, a lubricant, an inert diluent and/or a disintegrating agent.

In a preferred embodiment, the DIM-related indole is mixed with a binder, such as microcrystalline cellulose, and a surfactant, such as sodium lauryl sulphate until a homogeneous mixture is obtained. Subsequently, another binder, such as polyvinylpyrrolidone (polyvidone), is transferred to the mixture under stirring with a small amount of added water. This mixture is passed through granulating sieves and dried by desiccation before compression into tablets in a standard tableting apparatus.

A tablet may be coated or uncoated. An uncoated tablet may be scored. A coated tablet may be coated with sugar, shellac, film or other enteric coating agents.

Therapeutic formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soybean oil, mineral oil, sesame oil and the like. Formulations for parenteral administration also include a lyophilized powder comprising phytochemical that is to be reconstituted by dissolving in a pharmaceutically acceptable carrier that dissolves said phytochemical. Parenteral administration also includes a stable emulsion of DIM designed for intravenous use. Ideally, the emulsion prevents the early removal of DIM from the circulation due to early uptake by the reticulo-endothelial system allowing maximal cellular concentration of DIM in RSV-infected cells or tumor tissue.

When the pharmaceutical composition is a capsule, it may contain a liquid carrier, such as a fatty oil, e.g., cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides.

In yet another embodiment, the therapeutic compound can be delivered in a controlled release system. In one embodiment, a pump may be used (see Langer, supra; Sefton, CRC Crit. Ref. Biomed. Eng. 1987, 14:201; Buchwald et al., Surgery 1980, 88:507; Saudek et al., N. Engl. J. Med. 1989, 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J. Macromol. Sci. Rev. Macromol. Chem. 1983, 23:61; see also Levy et al., Science 1985, 228: 190; During et al., Ann. Neurol. 1989, 25:351; Howard et al., J. Neurosurg. 1989, 71:105).

Other controlled release systems are discussed in the review by Langer (1990, Science 249:1527-1533).

In one embodiment of the pharmaceutical composition according to the invention, the DIM-related indole and EGFR inhibitor are comprised as separate entities. The entities may be administered simultaneously or sequentially.

The invention also provides a pharmaceutical pack or kit comprising one or more containers filled with one or more of the ingredients of the pharmaceutical compositions of the invention. This includes the combination of capsules for oral use and creams or gels for simultaneous topical application. Optionally associated with such container(s) can be a notice in the form prescribed by a governmental agency regulating the manufacture, use or sale of pharmaceuticals or biological products, which notice reflects approval by the agency of manufacture, use or sale for human administration.

A number of references have been cited, the entire disclosures of which are incorporated herein by reference.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

6. EXAMPLES

6.1 Example

Manufacture of Processed DIM for Enhanced Oral Bioavailability

Preparation of processed Diindolylmethane is accomplished according to the steps outlined in U.S. Pat. No. 6,086,915, herein incorporated by reference in its entirety. Briefly, this included mixture of about 10-40% by final weight of Diindolylmethane with about 10-40% by final weight of vitamin E polyethylene glycol 1000 succinate (Vitamin-E-TPGS, Eastman Chemical), 2-20% by final weight, phosphatidyl choline (Phospholipon 50 G, Rhone Poulenc) and 15-30% by final weight hexanol. This mixture is made homogeneous by mixing. The homogeneous mixture of indoles and other oil soluble substituents listed above is added to a solution of modified starch in water (Capsul Starch from National Starch, Inc.). The starch component forms from 30-70% of the final dry weight of the product. The well dispersed final combined mixture is then subjected to spray drying. The resultant product is a fine powder containing Diindolylmethane contained within the starch particles.

6.2 Example

Manufacture of Capsules Containing Diindolylmethane

Capsules containing 150-300 mg of processed Diindolylmethane, as produced according to the steps described in example 6.1, are made by mixing the processed Diindolylmethane with microcrystaline cellulose and placing the mixed powder into opaque gelatin capsules.

Capsules containing the combination of 150 mg of processed Diindolylmethane and 30 mg of Resveratrol from 300 mg of Regrape X (Interpharma Praha, CZ), are made by mixing the processed Diindolylmethane, Regrape X, with microcrystaline cellulose or rice flour excipient and placing the mixed powder into opaque gelatin capsules.

6.3 Example

Manufacture of Cyclodextrin Complex Formulations with DIM-Related Indoles for Improved Bio-Delivery Introduction: As poorly soluble drug agents, DIM-related indoles require solubility enhancing formulation steps which are bio-compatible for parenteral and improved oral drug delivery. Parenteral formulations for intramuscular, intravenous, and pulmonary aerosol delivery benefit from complexation with various cyclodextrins (alpha-cyclodextrin, beta-cyclodextrin, hydroxypropyl-beta-cyclodextrin, and sulfobutylether-beta-cyclodextrin).

Methods: Specific formulations and formulation steps are developed utilizing cyclodextrins. Formulations are based on methods and observations that molecules containing indole rings successfully complex with cyclodextrins providing a subsequent solubility advantatage over the indole alone (Cao et al., 2000, Chemosphere 40:1411-6). Therefore, prototype formulation utilizing microcrystalline DIM, compatible solvent systems, with and without lipid stabilizers are manufactured using spray drying technology. Dry particle products are appropriate for suspension in aqueous vehicles for intramuscular or intravenous drug delivery.

Prefered Cyclodextrins Utilized Are:
1. β-cyclodextrin, which is generally more applicable for the complexation of hydrophobic molecules. It is anticipated that 2 molecules of β-cyclodextrin will be needed per molecule of DIM.
2. Hydroxypropyl β-cyclodextrin, which is known to be very soluble, on the order of 30% and more.
3. Sulfobutyl β-cyclodextrin (trade-name Captisol®). Captisol has a molecular weight of ~2200 mg/mmol so at 2:1 cyclodextrin to DIM, the amount of DIM that can be put into solution will be considerably higher than the known solubility of DIM.

Sample Preparations to be Undertaken:

Pharmaceutically acceptable solvents will be utilized to form solutions for spray drying with Hydroxypropyl β-cyclodextrin and Sulfobutyl β-cyclodextrin. Complexes of each of the β-cyclodextrins with DIM will be prepared with a slight excess of the cyclodextrin and spray dried to produce approximately 10 to 20 grams of each formulation. Further formulation suitable for intravenous, intramuscular and pulmonary aerosol use will utilize published manufacturing techniques (Steckel et al., 2004, Int J Pharm. 278:187-95).

Testing of Prepared DIM-Cyclodextrin Formulations:

Prepared samples will be analyzed as to amorphous crystal structure and stability using standard techniques (Rodriguez-Spong et al., 2004, Adv Drug Deliv Rev. 56:241-74). Testing of prepared formulations will include release testing of DIM in simulated gastric acid. In vivo release and bioavailability testing in animal and human models will utilize plasma DIM assays as described in U.S. Patent Application Publication No. 20030096855.

Conclusions: Cyclodextrin DIM Spray-dried formulations is expected to demonstrate shelf stability, form stable suspensions in 5% dextrose solutions for intravenous administration, and stable suspensions in 0.9% NaCl for intramuscular, parenteral administration.

6.4 Example

Manufacture of Aerosol Formulation of DIM for Treatment of RSV-Associated Conditions Typically, aerosol suspensions consist of microcrystalline DIM (0.01-0.25% or 0.01-0.5% wt/wt), and EDTA (0.15-1% wt/wt) suspended in an acceptable aerosol propellant consisting of chloroflurocarbons. These acceptable propellants include dichlorodifluromethhane, trichlorofluromethhane, with dehydrated alcohol USP or lecithin.

Alternatively, aerosol formulations containing DIM-related indoles are manufactured by adapting steps as described for ebselen, an unrelated but poorly soluble drug (U.S. Patent Application Publication No. 2004/0053888 A1). The resulting solution in sterile water will contain 3-6 grams of DIM per 100 ml of sterile water. The solution containing the DIM-cyclodextrin suspension is transferred to a clean, sterilized 500 ml SPAG-2 aerosol generator reservoir, diluted to a final volume of 300 ml with Sterile Water for Injection, USP. The aerosol is administered via endotracheal tube, mist mask, or vapor tent using published techniques (Newth et al., 1989, Pediatr Pulmonol. 7:183-8).

6.5 Example

Sterile Ophthalmic Emulsion of DIM for Treatment of RSV-Associated Ophthalmic Conditions Including Allergic Conjunctivitis Formulation of DIM for ophthalmic use is accomplished through manufacture of an emulsion designed for use as eye drops and for topical therapy of the conjunctiva. The emulsion is used to treat RSV related conjunctival infections and allergic conjunctival conditions alone and in conjunction with oral DIM. The ophthalmic emulsion is packaged in opaque, preservative-free, single use plastic vials/applicators.

A preferred ophthalmic emulsion consists of microcrystalline DIM (0.1-0.3% or 0.1-1.0%) (mean particle size 0.25 microns) as an active ingredient.

The composition of a preferred ophthalmic emulsion includes the following per ml: DIM (0.1%), glycerine, castor oil, polysorbate 80, carbomer 1342, purified water and sodium hydroxide to adjust the pH. Homogenization of these ingredients produces a translucent, homogeneous emulsion with a slightly pink color and with a pH of 6.0 to 7.5. Drops of the emulsion are applied 3 or more times daily to the effected eye. The unit dose vial is inverted a few times to disperse the emulsion before applying to the conjuctiva.

6.6 Example

Sterile Intravenous Microemulsions of DIM for Use in Conjunction with RSV Therapy Stable microemulsions of DIM, designed for intravenous use, are developed to provide a convenient means of administering DIM to achieve high tissue concentrations of DIM quickly and at a predictable time. This use facilitates the use of DIM in anti-viral therapy. In addition, microemulsions of DIM can be used in conjunction with other anti-viral agents, and with chemotherapy, radiation therapy, and combined chemoradiotherapy. Intravenous DIM can be used with topical iron/zinc chelators, with Epidermal Growth Factor inhibitors in RSV-associated conditions. In alternative embodiments, DIM analogues including imidazolelyl-3,3'-diindolylmethane, including nitro substituted imidazolelyl-3,3'-diindolylmethanes and DIM derivative SR13668 (Stanford Research Institute) can be used.

The low solubility of DIM in both water and lipid requires development of a specialized micro-emulsion that utilizes phospholipids to optimize the solubility of DIM and improve the stability of the microemulsion. To prepare the microemulsion Ethyl oleate (EO), Phosphatidyl Choline (PC) (from egg yolk), and calcein, are purchased from Sigma-Aldrich, Inc (St. Louis, Mo.). Distearoyl-phosphatidylethanolamin-N-poly(ethyleneglycol) 2000 (DSPE-PEG) is purchased from Avanti Polar Lipids (Alabaster, Ala.).

Using a modification of the method of Yu et al. (Yu et al., 1993, Int. J. Pharm. 89:139-146), the microemulsion is manufactured as follows: 160 grams of EO and 60 grams of PC are dissolved in 1 liter pure ethanol. 24 grams of microcrystalline DIM (mean particle size 0.25 micron) is added and dissolved in this "oily phase". 20 grams of DSPEG-PEG is then dissolved in 500 cc of USP water (Aqueous phase). The oily ethanolic solution (oily phase) with the dissolved DIM is then slowly added into the DSPE-PEG solution (aqueous phase) under moderate magnetic stirring. The aqueous phase immediately turned milky with opalescence as the result of the microemulsion produced. The microemulsion is then subjected to low pressure at 360 mm Hg and maintained at 50° C.

The low pressure is used to concentrate the emulsion through removal of the ethanol and a portion of the water. Using an infrared absorption assay to determine the DIM content of the microemulsion, a final concentration of DIM of 7.5 mg/ml is established. Sodium hydroxide is added to increase the pH to the 5.0-7.5 range.

Using this manufacturing technique emulsions of DIM are prepared and subjected to stability testing to demonstrate that the particle size within the emulsion remained between 150 and 200 nm. The production technique results in a microemulsion with % weight ranges of the components in the following preferred ranges:

| Component | Approx % Weight |
| --- | --- |
| DIM | 0.05-0.1 |
| Lipids (EO:PC:DSPE-PEG; 8:3:1) | 45-28 |
| Water | 50-70 |
| Ethanol | 1-2 |

Alternatively, an ethanol-free production method can be utilized to produce a stable micro-emulsion of DIM or DIM derivatives and analogues, using Lipofundin MCT B (Braun Melsungen AG, Melsungen, Germany), a preformed basic emulsion, and high pressure homogenization of microcrystalline DIM. This method utilizes jet-milled DIM, with particle size reduced to 0.1 micron average diameter (performed by Micron Technologies, Inc., Exton, Pa.). Using this technique 700 mg of 0.1 micron diameter DIM crystals are homogenized in 100 cc Lipofundin using equipment and methods as described (Akkar et al., 2003, Eur J Pharm Biopharm. 55:305-12). This results in a stable lipid-based microemulsion with particle size less than 200 nm and a DIM content of 7 mg/cc of the emulsion.

6.7 Example

Sterile Liposome-Encapsulated DIM for Topical, Intravenous and/or Pulmonary Targeting of DIM for Use in Conjunction with RSV Therapy Liposomes are microscopic vesicles composed of a phospholipid bilayer that encapsulate active agents for specialized delivery to specific tissues. In certain embodiments, liposome encapsulated DIM formulations are developed to provide increased concentration of DIM in respiratory and pulmonary tissue in RSV therapy. Manufacturing techniques for DIM Liposomes are developed based on the published liposome manufacturing techniques as described in U.S. Pat. Nos. 4,906,476; 5,006,343; and U.S. Patent Application Publication No. 20030108597, each of which is incorporated by reference herein in its entirety. The preferred techniques for producing DIM liposomes are those that result in liposomes which accumulate in lung and respiratory epithelial tissue.

Liposomes are formulated utilizing N-(carbonyl-methoxypolyethylene glycol 2000)-1,2disteaoyl-sn-glycero-3-phosphoethanolamine sodium salt (MPGEG-DSPE) (2-4 mg/ml); fully hydrogenated soy phosphatidylcholine (HSPC) (2-11 mg/ml); and cholesterol (1-4 mg/ml). Each 30 ml vial produced contains 30-60 mg of DIM-related indole at a concentration of 1-2 mg/ml.

DIM liposomes are utilized in hospitalized cases of RSV pneumonia every 8 to 12 hours. DIM liposomes are preferably administered intravenously or via aerosol using the SPAG-2 aerosol generator, via endotracheal tube, mist mask, or vapor tent using published techniques (Newth et al., 1989, Pediatr Pulmonol. 7:183-8).

6.8 Example

Apoptosis Promoting Activity of DIM in a Cell Culture Model Utilizing 4549 Airway Epithelial Cells Introduction: A549 airway epithelial cells provide a cell culture model which has been established as a culture system relevant to RSV infection and testing of in vivo interventions. Using A549 cells, cell culture studies demonstrated that DIM-related indoles induced accelerated rates of apoptosis in RSV infected cells and diminished production of new virus. In addition, the impact of DIM-related indoles and EGFR inhibitors on activation of cell survival signals including activation markers of intracellular Akt and Nuclear Factor kappa B (NFkappaB) can be assessed.

Cell Culture—A549 cells, a tumor cell line with properties of normal airway epithelial cells, were obtained from American Type Culture Collection (ATCC, Manassas, Va.) and incubated at 37° C. in 5% $CO_2$. The cells were cultured in Eagle's minimum essential medium (MEM, Invitrogen) supplemented with 10% fetal bovine serum (HyClone, Logan, Utah) and 40 mg/nil gentamicin. The A549 cells were subcultured by harvesting in 0.12% trypsin no more than 20 times from stock originally designated at pass 70. To minimize effects of exogenous growth factors or cytokines in this system, the supplemented serum concentration was reduced to 0.5% 24 h prior to and during all experiments with RSV infection. This serum supplement concentration slowed, but did not stop, cell division and showed no significant evidence of cytotoxicity at 72 h.

RSV Virus—RSV, strain A2, was obtained from Advanced Biotechnologies Inc. (Columbia, Md.) and was used directly as supplied for all experiments. The viral preparation was tested to have a $TCID_{50}$ titer of ~$1\times10^9$ in Hep-2 cells at 7 days. Sterile vials of the RSV preparation were supplied in MEM supplemented with 10% fetal calf serum, stored at −135° C. and rapidly thawed at 37° C. immediately prior to use. Cell culture techniques utilized for the A549 cells and controlled infection with RSV were performed using methods described in Thomas et al., 2002, J. Biol. Chem. 277:492-501, herein expressly incorporated by reference in its entirety.

Experimental Conditions Studied:

1. Uninfected A549 cells cultured for 36 hrs with DMSO (negative vehicle control)
2. Uninfected A549 cells cultured for 36 hrs, with added DIM, initially dissolved in DMSO (70, 210, and 700 nanomolar [nM] concentration in cell culture media).
3. A549 cells infected with RSV, strain A2, with DMSO (positive vehicle control)
4. A549 cells infected with RSV, strain A2, plus DIM initially dissolved in DMSO (70, 210, and 700 nanomolar [nM] concentration in cell culture media)
5. A549 cells infected with RSV, strain A2, plus LY294002 (2 and 5 micromolar [μM] concentration in cell culture media). Treated positive control using LY294002 as a chemical inducer of apoptosis.

Additional Experimental Conditions for Study:
6. A549 cells infected with RSV, strain A2, plus EGFR inhibitors at various concentrations (5-100 microgram/ml final concentration)
7. A549 cells infected with RSV, strain A2, plus EGFR inhibitors in combination with DIM at various concentrations (70, 210, and 700 nanomolar [nM] concentration in cell culture media)

Cell Viability and Death Assays—Induction of Apoptosis by DIM in RSV infected A549 cell was measured according to a Phosphohistone Assay. This included use of the H2A.X Phosphorylation Assay Kit (UpstateBiologicals, NY) which is a cell-based ELISA formatted for chemiluminescent detection. RSV-infected A549 cells, cultured as a monolayer, were removed from the culture wells, and the cells were immediately fixed with 95% EtOH-5% acetic acid and then with 1% formaldehyde in Tris-buffered saline (TBS). The formaldehyde solution was removed and the wells washed with 1× TBS plus 0.05% Tween 20 (TBST). The cells were blocked with 3% Bovine Serum Albumin (BSA) in TBS overnight at 4° C. and then probed with appropriate dilutions of anti-H2A.X mouse monoclonal antibody and then with detection antibody (goat anti-mouse HRP). The detection was done by LumiGLO™ chemiluminescent substrate and the plate was read in a microplate luminometer after 10-20 min. Luminescence indicated the extent of apoptosis in the sample examined. Results are summarized in FIG. 1.

Apotosis in RSV infected A549 cells cultured with and without DIM was further studied using the TUNEL assay for visualization of apoptosis. A549 cell monolayers that had been grown on coverslips were subjected to various treatments including exposure to physiologically relevant concentrations of DIM and infected with RSV. At various time points (hours post infection [hpi]), the monolayer was rinsed in PBS (phosphate-buffered saline) and fixed with ice-cold 10% trichloracetic acid for 15 min, followed by washes in cold 70%, 90%, and absolute ethanol for 3 min each. Apoptotic DNA fragments were end-labeled using the DeadEnd Fluorometric TUNEL System (Promega Inc.). After fixation, samples were again rinsed in PBS and incubated for 10 min with equilibration buffer (200 mM potassium cacodylate and 25 mM Tris-HCl, both pH 6.6, 0.2 mM DTT, 0.25 mg/ml BSA, and 2.5 mM $CoCl_2$). The enzymatic labeling reaction was performed for 60 min at 37° C. in the dark in the equilibration buffer supplemented with following reagents: 10 μM dATP, 1 mM Tris-HCl, pH 7.5, 0.1 mM EDTA, 5 μM fluorescein-12-dUTP and 25 units of TdT (final concentrations). To remove unincorporated dUTP, slides were washed three times 15 min each with 2×SSC and three times with PBS, and then viewed in a fluorescence microscope. Photomicrograph pictures were taken of each culture condition with the presence and intensity of fluorescent stain indicating active apoptosis in the examined cells. Photomicrographs from each culture condition were compared.

Levels of Production of Infectious RSV—Production of infectious RSV particles in A549 cell culture in the presence of various concentrations of DIM was measured using a method where the cell free media were titered for RSV infectious activity on a monolayer culture of Hep-2 cells. A549 monolayers in 12-well plates were infected with RSV and treated with DIM at the indicated concentrations. At 72 h post-infection, the media containing liberated progeny virus were collected from the wells and subjected to 10-fold serial dilutions in fresh media. The dilutions were plated on HEp-2 cell monolayers in 6-well plates, followed by agarose overlay at 6 hr. The plaques that appeared around 48 h of incubation were visualized by neutral red staining and counted. Results of averaged counts for each culture condition are presented in FIG. 2.

Levels of Intracellular RSV Growth—A real-time fluorescence measurement of live infected cells was utilized to determine the intracellular levels of RSV. Quantitation of real-time RSV growth in live cells was accomplished using a strain of RSV virus which produces florescent protein. Recombinant RSV virus producing green fluorescent protein (GFP) ('green RSV', abbreviated as 'gRSV') was kindly provided by Dr. Mark Peeples (Columbus Children's Res. Inst., Ohio). A549 cell monolayers were infected with the gRSV in the presence of indicated concentrations of DIM, and were periodically observed by fluorescence microscopy. For quantification, the fluorescence was measured in a standard plate-reader. Averaged results from each culture condition are presented in FIG. 3.

Additional methods—Cell death and cytotoxicity can also be measured by two additional methods: lactate dehydrogenase assay to quantify cellular lysis and an ethidium homodimer/calcein combined fluorescent assay to quantify membrane integrity and cell viability. For the lactate dehydrogenase assay cell culture, supernatants are aspirated, and the remaining adherent cells are lysed by addition of 0.1% Triton X-100 directly to each tissue culture well. Following incubation at 4° C. for 30 min, the supernatants and lysates are centrifuged to remove debris. After addition of phosphate buffer (0.1 M, pH 7.40), NADH (0.3 mM), and sodium pyruvate (0.6 mM), absorbance kinetics are measured at 340 nM. LDH activity in the supernatant is normalized to total LDH measured in supernatant plus lysate for each sample and expressed as percent of total activity, (i.e. % LDH activity=LDH activity supernatant/LDH activity supernatant+LDH activity cell lysate).

For a death and viability combined assay, a commercially available kit, the LIVE/DEAD® Viability/Cytotoxicity kit (Molecular Probes, Eugene, Oreg.) can be used in a 96-well microplate format. A549 cells are seeded in 96-well tissue culture plate at 20,000 cells/well and infected with adenoviral vector constructs as described below. After 36 h, the media are replaced with MEM at 0.5% and the cells cultured overnight. The cells are then exposed to various concentrations of DIM, EGFR drugs (Gefitinib, Erlotinib) or solvent control for 1 h followed by infection with RSV. Six, twelve or twenty four hours post-infection, the A549 cells are stained with 8 μM ethidium homodimer (EthD-1) for 15 min, and the fluorescence of EthD-1 bound to DNA in damaged cells is measured using 540±10 nm excitation filter and 620±10 nm emission filter on a Victor$^2$® (EG&G Wallac, Gaithersburg, Md.) microplate reader. The same cells are subsequently stained with 4 μm calcein acetoxymethyl ester (calcein-AM) for 30 min, and the fluorescence of calcein is measured using 485±8 nm excitation filter and 620±10 nm emission filter. Cell death and cell viability are expressed as relative fluorescence intensity of EthD-1 and calcein, respectively, after subtraction of background fluorescence from wells containing the fluorescent dyes in culture media and no cells.

In addition to cellular markers of apoptosis, treatment-related indicators of NFkappaB activation and cellular levels of phospho-Akt can be additionally assessed using double strand DNA probes and immunoblotting as described in published methods (Fiedler et al., 1996, J Virol. 70:9079-82; and Thomas et al., 2002, J Biol Chem. 277:492-501).

TUNEL Analysis and Flow Cytometry—Terminal deoxynucleotidyltransferase dUTP nick end labeling (TUNEL) analysis for DNA fragmentation can be carried out using an Apo-Direc™ kit obtained from PharMingen (San Diego, Calif.). Briefly, A549 cells are grown to 80% confluence in 100-mm tissue culture dishes, incubated 24 h in MEM supplemented with 0.5% fetal calf serum, and exposed to to various concentrations of DIM, EGFR drugs (Gefitinib, Erlotinib) or control solvent Me$_2$SO (1 µl/ml) for 1 h. RSV is added and the cells incubated for an additional 6 h. Cells are washed once with PBS and harvested by trypsinization. Cells in the washes and supernatants are pelleted and combined with the adherent fractions. The cells are fixed in 1% paraformaldehyde for 15 min and stored in 70% ethanol at −20° C. until staining and analysis. Cells are labeled with FITC-conjugated deoxyuridine triphosphate nucleotides and propidium iodide according to manufacturer's instructions and analyzed by flow cytometry (FACScan™, Becton Dickinson, San Jose, Calif.) using CELLQuest software, (Becton Dickson).

Results and Conclusions: Cell culture experiments revealed significantly accelerated cell death with evidence of apoptosis in RSV infected A549 epithelial cells treated with DIM. Photomicrographs from TUNEL stained A549 cells cultured with DIM at 210 and 700 nanomolar (nM) concentrations clearly showed earlier apoptosis at 12, 18, and 24 hours post infection (Data not shown). At 70, 210, and 700 nM concentrations, DIM treatment of RSV infected cells was associated with reduced intracellular RSV growth (FIG. 1), reduced production of infectious, progeny RSV virons (FIG. 2), accelerated apopotosis in RSV infected cells at 18 hrs of culture (FIG. 3), and activation of apoptosis specific Caspase-3 at less than 12 hrs of culture. Taken as a whole, the results indicated that DIM actively promoted early apoptosis in infected A549 cells, significantly inhibiting further growth and replication of RSV virus in cell culture. In contrast to the significant inhibition of RSV replication seen with DIM, chemical inhibitors of apopotosis caused increased RSV replication. The inhibition of RSV replication by DIM was equal or greater to that caused by LY294002, a chemical inducer of apoptosis and inhibitor of phosphatidylinosotide-3-kinase (PI-3K). The demonstrated reduction of viral replication through early apoptosis in human airway epithelial cells established relevant activity and mechanisms supporting therapeutic uses of DIM in RSV-related disease.

Further cell culture experiments are expected to reveal significantly accelerated cell death with evidence of apoptosis in RSV infected A549 epithelial cells treated with DIM-related indoles, EGFR inhibitors drugs, and the combination of DIM and EGFR inhibitors.

6.9 Example

In Vivo Demonstration of the Therapeutic Benefit of Parenteral DIM in Experimental Bovine Respiratory Syncytial Virus (bRSV) Infection Introduction: An experimental model for studying bRSV infection in calves has been used to demonstrate important aspects of viral replication and clearance (Viuff et al., 2002, Am J Pathol. 161:2195-207). Based on this well described method of laboratory-based, induced and monitored bRSV infection, five calves will be infected with bRSV and treated according to the following conditions in order to directly establish the efficacy of intervention with parenterally administered DIM, EGFR inhibitor, and the combination of DIM and EGFR inhibitor.

Treatment Protocol:
1. RSV infected, positive control animals treated with drug suspension vehicle only
2. RSV infected animal receiving DIM (15 mg/kg) from microencapsulated DIM (Example 6.1), added to feed starting 24 hrs before infection with RSV and continued for 5 days
3. RSV infected animal receiving DIM (5-15 mg/kg) intramuscularly every 12 hours for 5 days
4. RSV infected animal receiving DIM (5-15 mg/kg) intramuscularly every 12 hours for 7 days
5. RSV infected animal receiving Gefitinib (1-5 mg/kg) intramuscularly every 12 hours for 5-7 days
6. RSV infected animal receiving DIM (5-15 mg/kg) intramuscularly every 12 hours and Gefitinib (1-5 mg/kg) intramuscularly every 12 hours for 7 days Calves: Male Jersey calves (1 to 2 weeks of age) are derived from two closed herds and are kept in isolation until euthanasia. They are monitored weekly for IgM and IgG$_1$ antibodies to bRSV as described and they are free of clinical signs of respiratory tract disease at the time of inoculation. None of the calves will experience bRSV infection before inoculation. The calves will be inoculated at the age of ~3 months. A total of 5 calves are included in this study of which all are inoculated with bRSV. Inoculum are either lung wash fluid from a calf infected experimentally with a field isolate of bRSV or cell culture material of bRSV-infected fetal bovine lung cells. The calves are only inoculated once by combined intratracheal and aerosol route. A dose of $10^{4.6}$ (experiment IV) to $10^{5.2}$ tissue culture infectious dose$_{50}$ (TCID$_{50}$) diluted to 5 ml in phosphate-buffered saline (PBS) is administered throughout 10 minutes through a mask covering nostrils and mouth (Waechtomat inhalator VM 82, Kruse, Denmark, most droplets less than 3 µm). Subsequently, a dose of $10^{4.6}$ to $10^{5.2}$ TCID$_{50}$ diluted to 20 ml in PBS is injected into the trachea. All calves are housed together until the time of inoculation then the control calves are moved to separate, but similar isolation units.

Necropsy

The calves are anesthetized using pentobarbital and euthanized by exsanguination on PIDs 5 and 7-8. The lungs and trachea are immediately removed from the animals and photographs are taken of the ventral and dorsal sides of the lungs. The extent of consolidated lung tissue is scored from 0 to 5, in which the score of 0 is given to lungs completely free of lesions. The score of 1 is given to lungs with a few spots (1 to 5%) of consolidated lung tissue, 2 to lungs with 5 to 15%, 3 to lungs with 15 to 30%, and 4 to lungs with 30 to 50% of consolidated tissue. The score of 5 is given to lungs in which most of the tissue in the cranial, medial, and accessory lobes, and at least a third of the caudal lobes consisted of consolidated tissue (>50%).

Tissue samples from eight predetermined sites of the right lung, trachea, nasal epithelium, tonsilla palatina, and spleen are fixed in 10% neutral-buffered formalin.

Immunohistochemistry

Demonstration of bRSV antigen is performed on formalin-fixed tissue. Briefly, a biotinylated bovine anti-bRSV hyperimmuneserum is used as primary antibody followed by incubation with streptavidin and biotinylated alkaline phosphatase (K391; DAKO, Glostrup, Denmark). Fast Red (KemEnTec, Copenhagen, Denmark) is used as substrate and a biotinylated bovine anti-PI3 hyperimmuneserum served as negative control. Immunohistochemistry for detection of bRSV antigen is performed on all sections fixed in formalin from all of the animals. Immunohistochemistry on the lung sections is performed twice. To generate the score for the number of bRSV-positive cells, the whole section from the eight standardized areas of the lungs is evaluated. Three sections with different scores are used as internal control and are included in every batch of immunohistochemistry. The number of positive cells in the sections is estimated according to these three sections.

Double Immunohistochemistry

Detection of bRSV antigen is followed by demonstration of either epithelial cells or macrophages. bRSV antigen is visualized by incubation for 1 hour with biotinylated bovine anti-bRSV hyperimmuneserum followed by 30 minutes of incubation with streptavidin-β-galactosidase (Boehringer Mannheim, Mannheim, Germany). Sections are then incubated for 1 hour with X-Gal substrate (HistoMark, Kirkegaard & Perry Laboratories, Gaithersburg).

For demonstration of bRSV-positive epithelial cells, a monoclonal antibody against cytokeratin (MNF116, DAKO) is used. After development of the bRSV signal, as described above, sections are stored overnight in TBS at 4° C. followed by 5 minutes of protease treatment as described above and a 1-hour incubation with the primary antibody diluted 1:50 in TBS-NSS. Rabbit anti-mouse (Z259, DAKO) diluted 1:25 and alkaline phosphatase-anti-alkaline phosphatase complex (D651, DAKO) diluted 1:50 are used as secondary and tertiary antibodies, respectively, both incubated for 30 minutes. The sections are then incubated for 5 minutes with Fast Red (KernEnTec) and counterstained for 1 second in Harris' hematoxylin.

An anti-human-CD68 monoclonal antibody (EBM11, DAKO) is used as primary antibody for demonstration of bRSV-positive macrophages. Sections are kept overnight in TBS at 4° C. followed by 5 minutes of protease treatment and are then incubated overnight at 4° C. with anti-CD68 diluted 1:50 in TBS-NSS. The reaction is demonstrated with alkaline phosphatase-anti-alkaline phosphatase/Fast Red as described above for the cytokeratin staining. Double-positive cells are purple and could easily be differentiated from single-positive cells that are either clear blue (X-gal) or red (Fast Red).

In Situ Hybridization

The in situ hybridization is performed on formalin-fixed sections as previously described (Bryson D, 1993, Vet Med. 88:894-899). The probes are strand-specific RNA probes radiolabeled with $^{35}$S-UTP, and negative sense probes are used to demonstrate replication.

Demonstration of Apoptosis

An In Situ Cell Death Detection Kit AP from Boehringer Mannheim (terminal dUTP nick-end labeling reaction) is used to demonstrate apoptotic cells in formalin fixed tissue sections. After deparaffination, sections are treated with 10 µg/ml of proteinase K (Boehringer Mannheim) in 10 mmol/L of Tris, pH 7.5, and 2 mmol/L of $CaCl_2$ for 10 minutes at 37° C. The sections are rinsed twice with TBS, and then the protocol from the manufacturer is followed, except that TBS is used instead of PBS. The sections are developed with Fast Red (KemEnTec) for 10 minutes at room temperature.

Clinical Signs and Macroscopic Changes

Using this experimental model, as in naturally occurring bRSV infection, some individual differences in the severity of the disease will occur. Clinical signs of disease will range from mild coughing to a severe respiratory distress. Coughing, hyperpnea, tachypnea, and anorexia are the most prominent clinical features.

Based on prior experience with this animal model, the following schedule is utilized to assess the impact of intervention:

Sacrifice of an RSV infected and DIM treated calf at 5-7 days

Sacrifice of an RSV infected and DIM treated calf at 7-9 days

Sacrifice of an RSV infected and DIM plus EGFR treated calf at 7-9 days

Sacrifice of an RSV infected calf at 5-7 days

Sacrifice of an vehicle treated, RSV infected calve at 5-7 and 7-9 days

Results: Calves treated with DIM or DIM plus EGFR inhibitor drugs are expected to show less evidence of active bRSV infection than vehicle only treated positive control animals.

6.10 Example

In Vivo Treatment of RSV Infection Using Oral and Parenteral DIM in Balb/c Mice

Introduction: An in vivo model of RSV infection was utilized to demonstrate the therapeutic activity of DIM-related indoles in treating RSV infection and lung associated inflammation. The BALB/c mouse was chosen as a well established animal model, relevant for human RSV and parainfluenza virus infection (van Schaik et al., 1998, J Infect Dis. 177(2): 269-76). Previous work using this animal model has established the required viral innoculum, expected clinical signs, and pulmonary pathology following infection (Bitko et al., 2005, Nat Med. 11(1):50-5).

Another in vivo model of RSV infection has been developed using mice treated with cylphosphamide to induce immune deficiency and create a standardized receptive host for experimental infection (Sudo et al., 1999, Antivir Chem Chemother. 10:135-9). The technique provides for quantitation of pulmonary viral load following induced infection. This model can be used to assess the impact of daily intraperitoneal injections of DIM and/or an EGFR inhibitor drug (Gefitinib or Erlotinib) on in vivo RSV replication and induced pathology.

The Following Experimental BALB/c Groups and Treatment Protocol Using DIM were Studied:

1. RSV infected positive control group, infected with RSV and injected subcutaneously (SC) once daily with DMSO/Phosphate Buffered Saline (PBS) vehicle.
2. RSV infected, Low dose Parenteral DIM group (15 mg/kg/day), injected SC once daily with DIM suspension
3. RSV infected, High dose DIM Group (150 mg/kg/day), injected SC once daily with DIM suspension
4. RSV infected, orally treated DIM group (250 mg/kg/day from absorption enhanced DIM [Example 6.1]), added to powdered feed
5. Uninfected negative control group, nasally administered vehicle only, and injected subcutaneously (SC) once daily with DMSO/PBS vehicle Other Groups for Potential Study:

6. Low dose EGFR inhibitor group (0.5-3 mg/kg/day)
7. High dose EGFR inhibitor group (3-15 mg/kg/day)
8. DIM (5-25 mg/kg/day/day) plus Low dose EGFR inhibitor (0.5-3 mg/kg/day)

Experimental methods: Animal treatment methods followed those described in Bitko et al., 2005, Nat Med. 11(1): 50-5. Additional methods can be found in Sudo et al., 1999, Antivir Chem Chemother. 10:135-9.

Animals, cells, and viruses. Pathogen-free 8-10 week old female BALB/c mice, weighing between 16 and 20 g, were purchased from Charles River Laboratories. All mice were housed in cages covered with barrier filters and are fed mouse chow and water ad libitum. HeLa cells are maintained in Eagle's minimal essential medium supplemented with glutamine, gentamicin, penicillin G, and 10% fetal bovine serum.

RSV stock. RSV Long strain was grown on HEp-2 monolayers (American Type Culture Collection, Manassas, Va.). The extracellular media containing liberated progeny virus was collected at about 70 hr. The virus was purified and concentrated by precipitation with polyethylene glycol (MW 8,000) and sucrose gradient centrifugation. The final preparation had infectious titer in the range of $10^8$-$10^9$ pfu/ml and was stored frozen at −80° C. in small portions. All infectious viral titers (plaque forming units [pfu]) were determined by agarose plaque assay on HEp-2 monolayers with neutral red staining using standard procedures. Another suitable strain is the A2 strain of RSV (American Type Culture Collection).

Mouse treatment, infection and harvest. Intranasal application of RSV in BALB/c mice followed an established procedure (Bitko et al., 2005, Nat Med. 11(1):50-5) and causes predictable pulmonary disease and inflammation. For RSV infection, RSV stock was diluted such that each mouse was given $10^7$ pfu (plaque forming unit) of the virus intranasally.

Oral microencapsulated DIM (BioResponse Diindolylmethane, (BioResponse, LLC, Boulder, Colo. [Example 6.1]) was mechanically mixed with powdered feed. Microcrystalline DIM (BioResponse, LLC, Boulder, Colo.) was dissolved in DMSO and administered subcutaneously by injection as a suspension following rapid dilution in PBS. DIM was administered orally or subcutaneously into BALB/c mice (8-10 week old female, 16-20 g). The oral dose of DIM was maintained at roughly 250 mg/kg/day by monitoring food intake, offered ad libitum. SC injection of DIM suspension (15 mg/kg/day and 150 mg/kg/day) was administered once a day via alternate hind flanks. Both treatments were started 2 days before RSV infection, and were continued throughout the experimental protocol.

Alternatively, mice are treated intraperitoneally with 100 mg of cyclophosphamide (CYP) per kg of body weight 5 days before virus inoculation. The mice are weighed, anesthetized with sodium pentobarbital (50 mg/kg), and inoculated intranasally with approximately $10^5$ PFU of RSV A2 in 50 μl (day 0). From day 1 through day 3, the mice are exposed to the RD3-0028 or ribavirin aerosol. Placebo consisted of 10% DMSO-saline. On day 4, the day on which untreated mice will have the maximum RSV pulmonary titer, all animals are killed and the lungs of each mouse are removed.

Apoptosis-related assays. The lung homogenate was assayed by a Ac-DEVD-AFC protease assay employing a Ac-DEVD-AFC caspase-3 fluorogenic substrate (BD Biosciences, San Jose, Calif.) according the manufacturer's protocol, as described in a BD Pharmingen Technical Data Sheet for Catalog Number 556574, Rev. 004, Aug. 3, 2005.

Nucleosomes released in the cytoplasm during apoptosis were detected by a nucleosome ELISA assay kit (Calbiochem Nucleosome ELISA kit, Cat. No. QIA25, San Diego, Calif.) according to the manufacturer's protocol (User Protocol Q1A25 Rev. 28 Sep. 2005 RFH).

Pulmonary viral assay and clinical measurements. The animals were checked daily. Standard RSV symptoms were noted, including nasal mucus, increased respiratory rate due to congestion and bronchiolitis, a dull coat, ruffled fur and/or loss of fur, and a general lethargy and malaise. Respiratory rates (breaths per min) were determined by counting over a period of 2-3 mins. Sneezing, sniffing and sighing were excluded from counting. At various days post-infection (p.i.), lungs were removed for infectious virus assay and histopathology as described below.

To determine viral titer, the lung was homogenized in DMEM supplemented with 2% FBS (2 ml DMEM per 100 mg tissue) in cold. The extract was centrifuged at 2,000×g for 10 min, and serial dilutions of the supernatant were assayed for pfu. For pulmonary histopathology, the lungs were perfused and fixed in 10% buffered formalin and embedded in paraffin. Multiple, 4 μm thick sections were stained with haematoxylin & eosin (H&E) and scored for cellular inflammation under light microscopy by two independent researchers. Inflammatory infiltrates were scored by enumerating the layers of inflammatory cells surrounding the vessels and bronchioles. Zero to three layers of inflammatory cells were considered normal, whereas more than three layers of inflammatory cells surrounding 50% or more of the circumference of the vessel or bronchioles were considered abnormal. The number of abnormal perivascular and peribronchial spaces divided by total such spaces was the percentage reported as the pathology score. A total of about 20 spaces per lung were counted for each animal. With $10^7$ RSV infecting, about 30-35% of perivascular and peribronchial spaces could be found abnormal as early as Day 1 and peaked at Day 6. Bronchoalveolar lavage fluid (BALF) was collected by perfusing the bronchi and the lungs with 5×1.0 ml normal saline (containing 10 μg indomethacin per ml); total recovery of BALF per mouse was 4.2-4.4 ml. Samples containing visible signs of blood contamination were discarded. Cells were removed from BALF by centrifugation at 5,000×g for 15 min at 4° C., and samples stored at −80° C. until further analyses. The concentration of cysteinyl leukotrienes conjugates in the BALF was determined by an ELISA kit following the manufacturer's protocol (R&D Systems, Minneapolis, Minn.). According to the product insert, the cross-reactivity of the kit to the various leukotrienes was: LTC4 100%, LTD4 115%, LTE4 63% and LTB4 1.2%.

Alternatively, the removed lungs are homogenized with glass homogenizers with a Teflon pestle (Ikemoto Scientific Technology Co., Ltd., Tokyo, Japan) in 4 ml of Hanks balanced salt solution supplemented with 0.218 M sucrose, 4.4 mM glutamate, 3.8 mM $KH_2PO_4$, and 3.2 mM $K_2HPO_4$ as described previously (Piazza et al., 1993, J. Virol. 67:1503-1510). The resulting suspensions are stored at −70° C. prior to assay. HeLa cells are seeded into a 24-well tissue culture plate (Falcon 3074; Becton Dickinson, Lincoln Park, N.J.) at approximately $2\times10^5$ cells/well, and the plate is incubated at 37° C. in 5% $CO_2$. Lung homogenates from mice inoculated with strain A2 are diluted (10-fold) with Eagle's minimal essential medium supplemented with 2% fetal calf serum (Cell Culture Laboratories, Cleveland, Ohio), 100 U of penicillin G per ml, and 100 μg of streptomycin per ml. Each dilution of the homogenate is tested for the virus titer in confluent HeLa cells. After incubation for 5 days at 35° C., 80% methanol is added to the cell monolayer. The virus titers are assayed by plaquing. The wells are first incubated with 5% Fraction V in phosphate-buffered saline (PBS) for 30 min and then with horseradish peroxidase-conjugated anti-RSV serum (Virostat, Portland, Me.) diluted (20-fold) with 1% Fraction V in PBS for 1 h at 37° C. After washing twice with 5% Fraction V in PBS, the wells are then incubated with a 4 CN membrane peroxidase substrate (no. 50-73-00; Kirkegaard & Perry Laboratories Inc., Gaithersburg, Md.) at room temperature for optimal color development. The numbers of RSV plaques are counted.

Histologic methods and evaluation. Lungs are removed for histologic examination and are placed in buffered formalin for a minimum of 24 h. The tissue is then embedded in low-melting-point paraffin, sectioned at a 5-μm thickness, and stained with hematoxylin and eosin. The stained sections are coded by number and are evaluated blind as to the previous treatment. To determine lung condition, the lungs are assigned a score ranging from 0 (no pathology) to 4 (maximal pathology).

Results and Conclusions: DIM, administered orally or parenterally was shown to inhibit RSV growth in the lung (FIG. 3). In addition to significant reduction in viral counts in lung tissue, treated animals showed evidence of increased apoptosis in lung tissue homogenate (FIG. 4), significantly reduced disease severity as reflected in a normalized respiratory rate at day 6 p.i. (FIG. 5) and reduced severity in lung pathology (FIG. 6). Efficacy of DIM treatment to reduce RSV-induced lung inflammation was indicated by significant reduction in leukotriene levels in Bronchoalveolar Lavage Fluid (BALF) seen only in DIM-treated animals (FIG. 7).

The results in the in vivo BALB/c mouse studies establish the utility and efficacy of DIM-related indoles as a therapeutic modality for RSV-related disorders in vertebrates. Utilization of intravenous preparations of DIM in RSV infection is expected to provide even greater efficacy since greater plasma DIM levels will be achieved and DIM is known to be concentrated in lung tissue (Anderton et al., 2004, Drug Metab Dispos. 32:632-8). Reduction in pulmonary leukotriene levels at 6 and 10 days p.i. in BALB/c mice indicates that DIM therapy can reduce the post infectious, RSV-related inflammation associated with chronic wheezing and asthma in humans.

Treatment of cyclophosphomide pre-treated mice with DIM, EGFR inhibitors and the combination of EGFR inhibitors is expected to result in a reduction of pulmonary RSV titers and reduced pathology score on histologic examination as compared with the vehicle treated placebo group.

6.11 Example

Observational Study of the Prophylactic Use of Oral DIM for the Treatment and Prevention of RSV Introduction: Clinical data on frequency and severity of RSV infections will be monitored with and without DIM therapy in a pilot clinical study. The objective is to observe details of acute severity and rates of RSV transmission to siblings of pediatric patients. Additionally, the occurrence and persistence of chronic pulmonary symptoms such as wheezing, bronchitis, and further infections will be monitored.

Study Plan: An observational study will be conducted by collaborating pediatricians and parents during the Winter RSV season. The objective of the study is to assess the impact of oral, absorption-enhanced DIM use by symptomatic RSV patients and their siblings. Index cases of RSV infection will have the diagnosis of RSV confirmed through viral-specific testing for RSV antigens on nasal swabs (Directogen-RSV, Becton Dickinson, USA). Alternatively, collection of nasal aspirates and application of the RSV "Respi-Strip" will be used to identify index cases utilizing well described methods (Gregson et al., 2005, J Clin Microbiol. 43(11):5782-3).

Treatment with oral, absorption-enhanced DIM (Example 6.1) providing 1-4 or 1-7 mg/kg/day) will be started by the symptomatic patient and all siblings and continued on a twice a day schedule for one week. Symptom scores for the patient and each sibling will be recoreded on a daily basis for 2 weeks using a symptom diary. A control group of RSV patients and their siblings, matched as close as possible to the age of DIM treatment cases and age of siblings, similar school or childcare environment, and/or other RSV-related variable, will also be recruited to form a comparison, control group. The control group will receive supportive care without DIM treatment. In both DIM treatment and supportive care only groups, the DIM-treated and supportive care only families will prospectively complete the same symptom diary form for index patients and siblings.

Data from symptom diaries will be compared for the DIM treatment and supportive care groups to assess impact of the DIM treatment on severity of symptoms, spread and severity of infectious symptoms to siblings, duration of symptoms, and requirements for additional therapy over 1 month including, use of brochodilators, antibiotics, doctor visits, and hospitalizations.

Results: Based on prospective symptom diaries, intervention with absorption enhanced DIM is expected to result in reduction of severity of symptoms in DIM-treated index cases of RSV compared to untreated RSV cases. Also expected are reduced severity of RSV-related symptoms and shorter duration of RSV-related symptoms in DIM-treated subjects and their DIM-treated siblings compared to untreated, supportive care only RSV cases and their siblings.

What is claimed is:

1. A method of treating an RSV infection comprising administering to a subject having an RSV infection a therapeutically effective amount of one or more DIM-related indoles.

2. The method of claim 1, wherein the DIM-related indole is selected from the group consisting of 3,3'-diindolylmethane (DIM), hydroxylated DIMs, methoxylated DIMs, 2-(indol-3-ylmethyl)-3,3'-diindolylmethane (LTR), hydroxylated LTRs, methoxylated LTRs, 1-(3-hydroxymethyl)-indolyl-3-indolymethane (HI-IM), 5,5'-dimethylDIM (5-Me-DIM), 2,2'-dimethylDIM (2-Me-DIM), 5,5'-dichloroDIM (5-Cl-DIM), imidazolelyl-3,3'-diindolylmethane, nitro-substituted imidazolelyl-3,3'-diindolylmethanes, 2,10-dicarbethoxy-6-methoxy-5,7-dihydro-indolo-[2,3-b]carbazole, 6-ethoxycarbonyloxy-5,7-dihydro-indolo-[2,3-b]carbazole and 2,10-dicarbethoxy-6-ethoxycarbonyloxy-5,7-dihydro-indolo-[2,3-b]carbazole, and 2,6-dicarbethoxy-3,3'-dimethyl-13,14-diindolylmethane.

3. The method of claim 2, wherein the DIM-related indole is DIM.

4. The method of claim 3, wherein the DIM is processed DIM.

5. The method of claim 1, wherein the DIM-related indole is indole-3-carbinol (I3C).

6. The method of claim 1, wherein the RSV infection is an acute RSV infection.

7. The method of claim 6, wherein the acute RSV infection is selected from the group consisting of pharyngitis, croup, bronchiolitis and pneumonia.

8. The method of claim 1, wherein said subject is a human.

9. The method of claim 1, wherein said subject is a cow.

10. The method of claim 1, wherein said subject is a bird.

11. The method of claim 1, wherein the DIM-related indole is administered orally.

12. The method of claim 1, wherein the DIM-related indole is formulated as a tablet, pill, capsule, suppository cream, parenteral suspension or liposomal spray or is suspended as microparticles in a starch carrier matrix.

13. The method of claim 3, wherein the DIM is formulated as a parenteral suspension.

14. The method of claim 5, wherein the I3C is formulated as a parenteral suspension.

15. The method of claim 1, wherein the DIM-related indole is formulated for aerosol administration, ophthalmic administration, intranasal administration, intrapulmonary administration, intravenous administration, intramuscular administration, vaginal administration, rectal administration or topical administration.

16. The method of claim 1, wherein the DIM-related indole is administered intravenously.

17. The method of claim 3, wherein the DIM is administered intravenously.

18. The method of claim 5, wherein the I3C is administered intravenously.

19. The method of claim 1, wherein the DIM-related indole is administered with a differentiation promoting agent.

20. The method of claim 19, wherein said differentiation promoting agent is selected from the group consisting of vitamin D, calcitriol, vitamin A, a retinoid derivative, and a macrophage colony stimulating factor.

21. The method of claim 1, wherein the DIM-related indole is administered with an endoplasmic reticulum stress inducer.

22. The method of claim 1, wherein the DIM-related indole is administered with a RSV anti-viral drug selected from the group consisting of an RSV-vaccine, anti-RSV immunoglobulin, hAnti F-glycoprotein, anti-RSV monoclonal antibody, plant flavinoid, benzoditin, ribavirin, ganciclovir, valganciclovir, cidofovir, and phosphocarnet.

23. The method of claim 1, wherein the DIM-related indole is administered with an immune stimulating beta glucan.

24. The method of claim 1, wherein the DIM-related indole is administered with resveratrol.

\* \* \* \* \*